(12) United States Patent
Kuwabara et al.

(10) Patent No.: US 8,357,908 B2
(45) Date of Patent: Jan. 22, 2013

(54) RADIATION DETECTING CASSETTE AND RADIATION IMAGE PICKING-UP SYSTEM

(75) Inventors: Takeshi Kuwabara, Minami-ashigara (JP); Eiichi Kito, Minami-ashigara (JP); Tsuyoshi Tanabe, Odawara (JP); Takuya Yoshimi, Yokohama (JP); Kazuharu Ueta, Tokyo (JP); Makoto Iriuchijima, Gunma-ken (JP); Yasunori Ohta, Yokohama (JP)

(73) Assignee: Fujifilm Corporation, Tokyo (JP)

( * ) Notice: Subject to any disclaimer, the term of this patent is extended or adjusted under 35 U.S.C. 154(b) by 392 days.

(21) Appl. No.: 12/452,864

(22) PCT Filed: Jul. 2, 2008

(86) PCT No.: PCT/JP2008/061949
§ 371 (c)(1),
(2), (4) Date: Mar. 18, 2010

(87) PCT Pub. No.: WO2009/016909
PCT Pub. Date: Feb. 5, 2009

(65) Prior Publication Data
US 2010/0187427 A1    Jul. 29, 2010

(30) Foreign Application Priority Data

Jul. 27, 2007   (JP) ................. 2007-195539
Jul. 30, 2007   (JP) ................. 2007-197243
Jul. 30, 2007   (JP) ................. 2007-197948

(51) Int. Cl.
*H01L 27/146* (2006.01)
(52) U.S. Cl. ................................. 250/370.08
(58) Field of Classification Search .............. 250/370.01–370.15; 378/98.8
See application file for complete search history.

(56) References Cited

U.S. PATENT DOCUMENTS

| | | | |
|---|---|---|---|
| 5,877,501 A * | 3/1999 | Ivan et al. | ................. 250/370.09 |
| 5,894,129 A | 4/1999 | Pool | |
| 6,801,598 B2 | 10/2004 | Tashiro et al. | |
| 6,972,410 B2 | 12/2005 | Takeda | |
| 7,541,591 B2 | 6/2009 | Endo et al. | |
| 7,622,889 B2 * | 11/2009 | Spahn | ............................ 320/101 |
| 2006/0280337 A1 | 12/2006 | Iwakiri et al. | |

FOREIGN PATENT DOCUMENTS

| | | |
|---|---|---|
| JP | 3494683 | 6/1995 |
| JP | 9-107503 | 4/1997 |
| JP | 11-128213 A | 5/1999 |
| JP | 2000-105297 | 4/2000 |
| JP | 2001-224579 | 8/2001 |
| JP | 2002-191586 | 7/2002 |
| JP | 2002-214729 | 7/2002 |

(Continued)

*Primary Examiner* — Kiho Kim
(74) *Attorney, Agent, or Firm* — Jean C. Edwards, Esq.; Edwards Neils PLLC

(57) ABSTRACT

A wireless communication control unit controls a transmitting and receiving apparatus so as to prohibit transmission of radiation image information to the outside by wireless communication or power supply from the outside to an electric power source by wireless communication in accordance with an exposure detecting signal from an exposure detecting unit or a conversion detecting signal from a conversion detecting unit. Thus, this can control the transmitting and receiving apparatus not to carry out, at the same period of time, the irradiation of a radiation (X) to a radiation detector, a conversion operation of the radiation image information in the radiation detector, and wireless communication by the transmitting and receiving apparatus.

16 Claims, 14 Drawing Sheets

FOREIGN PATENT DOCUMENTS

| | | |
|---|---|---|
| JP | 2003-121553 | 4/2003 |
| JP | 2003-126072 | 5/2003 |
| JP | 2003-210444 | 7/2003 |
| JP | 2004-180931 | 7/2004 |
| JP | 2006-68507 A | 3/2006 |
| JP | 2006-087566 | 4/2006 |
| JP | 2006-141170 A | 6/2006 |
| JP | 2006-247102 | 9/2006 |
| JP | 2006-263322 A | 10/2006 |
| JP | 2006-334281 | 12/2006 |
| JP | 2007-151761 | 6/2007 |
| WO | WO/2006-101234 A1 | 9/2006 |

* cited by examiner

RADIATION DETECTING CASSETTE AND RADIATION IMAGE PICKING-UP SYSTEM

CROSS-REFERENCE TO RELATED APPLICATIONS

The present invention is a 35 USC 371 national stage entry of PCT/JP2008/061949, filed Jul. 2, 2008, which claims priority from Japanese Patent Application No. 2007-195539, filed Jul. 27, 2007, Japanese Patent Application No. 2007-197243, filed Jul. 30, 2007, and Japanese Patent Application No. 2007-197948, filed Jul. 30, 2007, the contents of all of which are herein incorporated by reference in their entirety.

TECHNICAL FIELD

The present invention relates to a radiation detecting cassette having a radiation conversion panel for detecting radiation that has passed through a subject and converting the detected radiation into radiographic image information, a radiographic image capturing (radiation image picking-up) system incorporating such a radiation detecting cassette therein, and a radiographic image capturing (radiation image picking-up) system including such a radiation detecting cassette and a power feeder for wirelessly supplying electric power to the radiation detecting cassette.

BACKGROUND ART

In the medical field, radiation image capturing apparatus have widely been used, which apply radiation to a subject and guide the radiation that has passed through the subject to a radiation conversion panel, which captures a radiation image from the radiation. Known forms of radiation conversion panels include a conventional radiation film for recording a radiation image by way of exposure, and a stimulable phosphor panel for storing radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device to read the radiation image as a visible image.

In an operating room or the like, it is necessary to read a recorded radiographic image immediately from a radiation conversion panel after the radiographic image has been captured, for the purpose of quickly and appropriately treating the patient. As a radiation conversion panel that meets such a requirement, a radiation detector has been developed having a solid-state detector for converting radiation directly into electric signals, or converting radiation into visible light with a scintillator and then converting the visible light into electric signals in order to read a detected radiographic image.

When the radiation conversion panel detects radiation and converts the detected radiation into radiographic image information, the radiation conversion panel outputs signals representative of the radiographic image information. Since the signals output from the radiation conversion panel are low in level and susceptible to electromagnetic noise, the quality of radiographic images generated based on such signals tends to be reduced if electromagnetic noise is added to the signals.

Patent Document 1 proposes that capturing of radiographic images and performing wireless communications from a radiation detecting cassette to an external circuit should not be performed at the same time. Patent Documents 2 and 3 propose that a battery and a radiation conversion panel are separated by a partition plate having an electromagnetic shielding capability, which is disposed in a radiation detecting cassette.

If wireless communications are performed between a radiation detecting cassette and an external circuit while a radiographic image of a subject is being captured, then electromagnetic noise, which is caused by the radiation applied to the radiation detecting cassette through the subject, and electromagnetic noise, which is caused by an address signal and a control signal used by the radiation detecting cassette to convert the radiation into radiographic image information, are added to signals that are sent and received by way of wireless communications, tending to lower the quality of the radiographic image information. When electric power is supplied to a battery (power supply) in the radiation detecting cassette by way of wireless communications, if the aforementioned electromagnetic noise is added to the electric power supplied to the battery, then the radiation detecting cassette and the wireless communications means, which are powered by the battery, are likely to malfunction.

According to Patent Document 1, however, no countermeasures are taken to prevent electromagnetic noise from being added to the electric power that is supplied from an external circuit to the battery. According to Patent Documents 2 and 3 as well, no countermeasures are taken to prevent the addition of electromagnetic noise.

Patent Document 4 discloses a radiation detecting cassette for transmitting radiographic image information produced by a radiation detector to an image processing means utilizing a wireless transmission system. A battery disposed in the radiation detecting cassette is wirelessly charged by a contactless battery charger, which is located close to the battery.

When the remaining power level of the battery runs low while the radiation detecting apparatus is being used (while radiographic image information is being captured), it is necessary that the image capturing process be interrupted and that the battery be charged by the contactless battery charger. To charge the battery, the operator places the contactless battery charger near the battery of the radiation detecting cassette, and operates a manual switch or the like. As a result, if the radiation detecting cassette is used during a surgical operation, particularly, the doctor is unable to see the desired radiographic image in real time, and the process for charging the battery is cumbersome and time-consuming.

The radiation detecting cassette, which is wirelessly charged, needs to remain available for charging the battery at all times, or needs to have a switch for initiating charging of the battery. In the former case, wasteful power consumption and malfunctions are likely to occur. In the latter case, the process is cumbersome, and further, the battery will not be charged if the operator forgets to operate the switch.

Patent Document 4 also discloses a technique for charging a battery, in which a power cable is connected to the battery while the battery is dismounted and connected to an external battery charger.

Radiographic image information generated by the radiation detector is transmitted to the image processing means by way of wireless communications. Such radiographic image information, which is transmitted by wireless communications, is susceptible to radio disturbance and noise. When the radiographic image information suffers from radio disturbance, radiographic images generated thereby may not appropriately be displayed.

According to Patent Document 4, furthermore, inasmuch as the radiation detecting cassette depends only on the battery for energization thereof, if the remaining power level of the battery runs too low while the radiation detecting apparatus is being used (while radiographic image information is being captured), the image capturing process must be interrupted in order to charge the battery using the contactless battery charger. As a result, if the radiation detecting cassette is used during a surgical operation, particularly, the doctor is unable to see desired radiographic images in real time.

Cables that may be connected to the radiation detecting cassette should desirably be as minimal as possible, in view of facilitating handling thereof in an operating room or the like.

Patent Document 1: Japanese Laid-Open Patent Publication No. 2003-210444

Patent Document 2: Japanese Laid-Open Patent Publication No. 2002-214729

Patent Document 3: Japanese Laid-Open Patent Publication No. 2003-121553

Patent Document 4: Japanese Laid-Open Patent Publication No. 2001-224579

DISCLOSURE OF THE INVENTION

A first object of the present invention is to provide a radiation detecting cassette and a radiographic image capturing system, which are capable of reliably removing the effects of electromagnetic noise when radiographic image information is transmitted from the radiation detecting cassette to an external circuit by way of wireless communications, and when electric power is supplied from an external circuit to a power supply of the radiation detecting cassette by way of wireless communications.

A second object of the present invention is to provide a radiographic image capturing system and a radiation detecting cassette, which are capable of increasing ease of handling the radiation detecting cassette when electric power is supplied thereto, avoiding interruptions of an image capturing process due to a shortage in the remaining power level of a battery of the radiation detecting cassette, and of preventing wasteful power consumption and malfunctions.

A third object of the present invention is to provide a radiographic image capturing system, which is capable of transmitting radiographic image information generated by a radiation conversion panel of a radiation detecting cassette to an image processing means highly accurately and precisely, and of increasing ease of handling the radiation detecting cassette.

To achieve the first object, there is provided a radiation detecting cassette comprising:

a radiation conversion panel for detecting radiation that has passed through a subject and converting the detected radiation into radiographic image information;

wireless communicating means for performing wireless communications with an external circuit;

wireless communications control means for controlling the wireless communicating means;

exposure detecting means for detecting application of the radiation to the radiation conversion panel and outputting a detected result as an exposure detection signal to the wireless communications control means;

conversion detecting means for detecting conversion into the radiographic image information by the radiation conversion panel and outputting a detected result as a conversion detection signal to the wireless communications control means; and a power supply for energizing the radiation conversion panel, the exposure detecting means, the conversion detecting means, the wireless communicating means, and the wireless communications control means, wherein the wireless communications control means controls the wireless communicating means to inhibit transmission of the radiographic image information to an external circuit by way of the wireless communications and/or supply of electric power from an external circuit to the power supply by way of the wireless communications.

According to the present invention, the wireless communications control means controls the wireless communicating means in order to inhibit transmission of the radiographic image information to an external circuit by way of wireless communications and/or to inhibit the supply of electric power from an external circuit to the power supply by way of wireless communications, based on the exposure detection signal from the exposure detecting means and the conversion detection signal from the conversion detecting means.

The wireless communicating means can thus be controlled so as not to perform application of radiation to the radiation conversion panel and/or conversion into the radiographic image information by the radiation conversion panel, within a same time zone during which wireless communications by the wireless communicating means are carried out. As a result, electromagnetic noise caused by application of radiation, as well as electromagnetic noise caused by the conversion operation of the radiation conversion panel, are reliably prevented from being added to the radiographic image information, which is transmitted to an external circuit by way of wireless communications, and to the electric power supplied from an external circuit to the power supply by way of wireless communications. The effect of such electromagnetic noise during wireless communications can reliably be removed according to the present invention.

To achieve the second object, there is provided a radiographic image capturing system comprising:

a radiation detecting cassette including a radiation conversion panel for detecting radiation that has passed through a subject and converting the detected radiation into radiographic image information, and transmitting means connected to the radiation conversion panel, for transmitting the radiographic image information to an image processing means, and a power feeder for wirelessly feeding power to the radiation detecting cassette;

wherein the power feeder includes electric power transmitting means for converting electric energy and wirelessly supplying the converted energy to the radiation detecting cassette;

the radiation detecting cassette includes an energy converter for converting the energy supplied from the electric power transmitting means back into electric energy; and the electric power transmitting means is disposed in a state for wirelessly feeding power to the energy converter of the radiation detecting cassette, which is disposed in a state for capturing a radiographic image of the subject.

With the above arrangement, the power feeder is disposed in a position capable of wirelessly feeding power to the radiation detecting cassette at all times when the radiation detecting cassette is being used (when a radiographic image is captured). Therefore, the radiographic image capturing system can capture radiographic images without requiring power cables to be connected to the radiation detecting cassette. Not only the radiation detecting cassette, but also the system as a whole, can be handled with ease. Furthermore, the process of capturing radiographic images, as well as the surgical operation, effectively is prevented from becoming interrupted due to an excessively low remaining power level in the battery of the radiation detecting cassette.

To achieve the second object, there is also provided a radiographic image capturing system comprising:

a radiation detecting cassette including a radiation conversion panel for detecting radiation that has passed through a subject and converting the detected radiation into radiographic image information, and transmitting means connected to the radiation conversion panel, for transmitting the radiographic image information to an image processing means; and a power feeder for wirelessly feeding power to the radiation detecting cassette, wherein the power feeder includes an electric power transmitting means for converting electric energy, and for wirelessly supplying the converted energy to the radiation detecting cassette, and further wherein the radiation detecting cassette includes an energy converter for converting the energy supplied from the electric power transmitting means back into electric energy, and an electric power reception on/off detector for detecting whether the radiation detecting cassette has been placed in an area capable of receiving energy supplied from the electric power transmitting means.

With the above arrangement, since the radiation detecting cassette includes the electric power reception on/off detector, when the radiation detecting cassette is placed in the feeding area of the power feeder, the radiation detecting cassette and the power feeder automatically exchange information with each other, whereby the radiation detecting cassette is brought into a state capable of capturing radiographic images. Consequently, the radiation detecting cassette does not need to be activated in a preparatory state for enabling capturing of radiographic images, using a battery, etc., and the radiation detecting cassette is not required to have a manual power supply switch. Wasteful power consumption and malfunctioning are avoided, and the surgeon or a radiological technician is prevented from making mistakes, such as failing to capture a radiographic image by forgetting to operate a manual power supply switch. Accordingly, the radiographic image capturing system including the radiation detecting cassette can be handled with greater ease.

If the radiation detecting cassette includes a battery for storing electric energy converted back by the energy converter, then since the radiation detecting cassette can utilize electric power supplied from the power feeder as well as electric power supplied from the battery, the radiation detecting cassette can be energized with increased stability.

If the radiation detecting cassette includes a controller for instructing the energy converter to start converting the energy back into electric energy when the electric power reception on/off detector detects that the radiation detecting cassette has been placed in an area capable of receiving energy supplied thereto from the electric power transmitting means, then wasteful power consumption is avoided, because the radiation detecting cassette does not need to be kept energized at all times.

If the radiographic image capturing system further comprises a power supply selector for selecting the battery as a power supply for energizing the radiation detecting cassette when the electric power reception on/off detector detects that the radiation detecting cassette has been placed outside of the area capable of receiving energy supplied from the electric power transmitting means, then the radiation detecting cassette can continuously be used in the event that the power feeder malfunctions or fails to operate.

If the radiographic image capturing system further comprises an indicator for externally indicating that the electric power reception on/off detector has detected the radiation detecting cassette being placed outside of the area capable of receiving energy supplied from the electric power transmitting means, then malfunctioning of the power feeder, etc., can quickly be indicated to a surgeon or the like.

To achieve the second object, there also is provided a radiation detecting cassette comprising:

a radiation conversion panel for detecting radiation that has passed through a subject and converting the detected radiation into radiographic image information;

transmitting means connected to the radiation conversion panel, for transmitting the radiographic image information to an image processing means; an energy converter for converting wirelessly supplied energy converted from electric energy back into electric energy; and an electric power reception on/off detector for detecting whether the radiation detecting cassette has been placed in an area capable of receiving wirelessly supplied energy.

To achieve the third object, there is also provided a radiographic image capturing system comprising:

a radiation detecting cassette including a radiation conversion panel for detecting radiation that has passed through a subject and converting the detected radiation into radiographic image information, and transmitting means connected to the radiation conversion panel, for transmitting the radiographic image information to an image processing means; and a power feeder for feeding power to the radiation detecting cassette, wherein the transmitting means transmits the radiographic image information to the image processing means in a wired fashion through a signal line; and the power feeder wirelessly feeds power to the radiation detecting cassette.

With the above arrangement, the radiographic image information acquired by the radiation conversion panel of the radiation detecting cassette is transmitted in a wired fashion through the signal line, whereas the radiation detecting cassette is fed power wirelessly by the power feeder. Consequently, the transmitted radiographic image information is reliably prevented from being affected by radio disturbance and noise from other electronic devices, so that radiographic images can be generated highly accurately and precisely. Since the radiation detecting cassette is fed power wirelessly, the cables connected to the radiation detecting cassette can be kept at a minimum, and hence the radiation detecting cassette can be handled with increased ease, while at the same time the radiation image is prevented from becoming degraded. Since the radiation detecting cassette is fed power wirelessly at all times, the process of capturing radiographic images as well as the surgical operation are prevented from being interrupted due to an excessively low remaining power level in the battery of the radiation detecting cassette.

If the power feeder includes an electric power transmitting means for converting electric energy and wirelessly supplying the converted energy to the radiation detecting cassette, and the radiation detecting cassette includes an energy converter for converting the energy supplied from the electric power transmitting means back into electric energy, and an electric power reception on/off detector for detecting whether the radiation detecting cassette has been placed in an area capable of receiving energy supplied from the electric power transmitting means, then a system is established in which it can automatically be detected that the radiation detecting cassette has been placed in a feeding area of the power feeder, for example.

If the radiation detecting cassette includes a data control means for receiving identification data of the power feeder and for transmitting a wireless feeding enable signal to an external control device via the transmitting means and the signal line when the electric power reception on/off detector detects that the radiation detecting cassette has been placed in an area capable of receiving energy supplied from the electric power transmitting means, and if the control device receives the wireless feeding enable signal from the radiation detecting cassette and thereafter transmits a power feeding start signal to the power feeder, which corresponds to the identification data, then when the radiation detecting cassette is placed in the feeding area of the power feeder, the radiation detecting cassette and the power feeder automatically exchange information, and the radiation detecting cassette is energized into a state for enabling capturing of radiographic images. Even when a plurality of power feeders is installed, a desired one of the power feeders can appropriately and selectively feed power to the radiation detecting cassette. Therefore, the radiographic image capturing system as a whole, including the radiation detecting cassette, can be handled with increased ease.

BEST MODE FOR CARRYING OUT THE INVENTION

A radiographic image capturing system 10A according to a first embodiment will be described below with reference to FIGS. 1 through 4.

Figure 1:
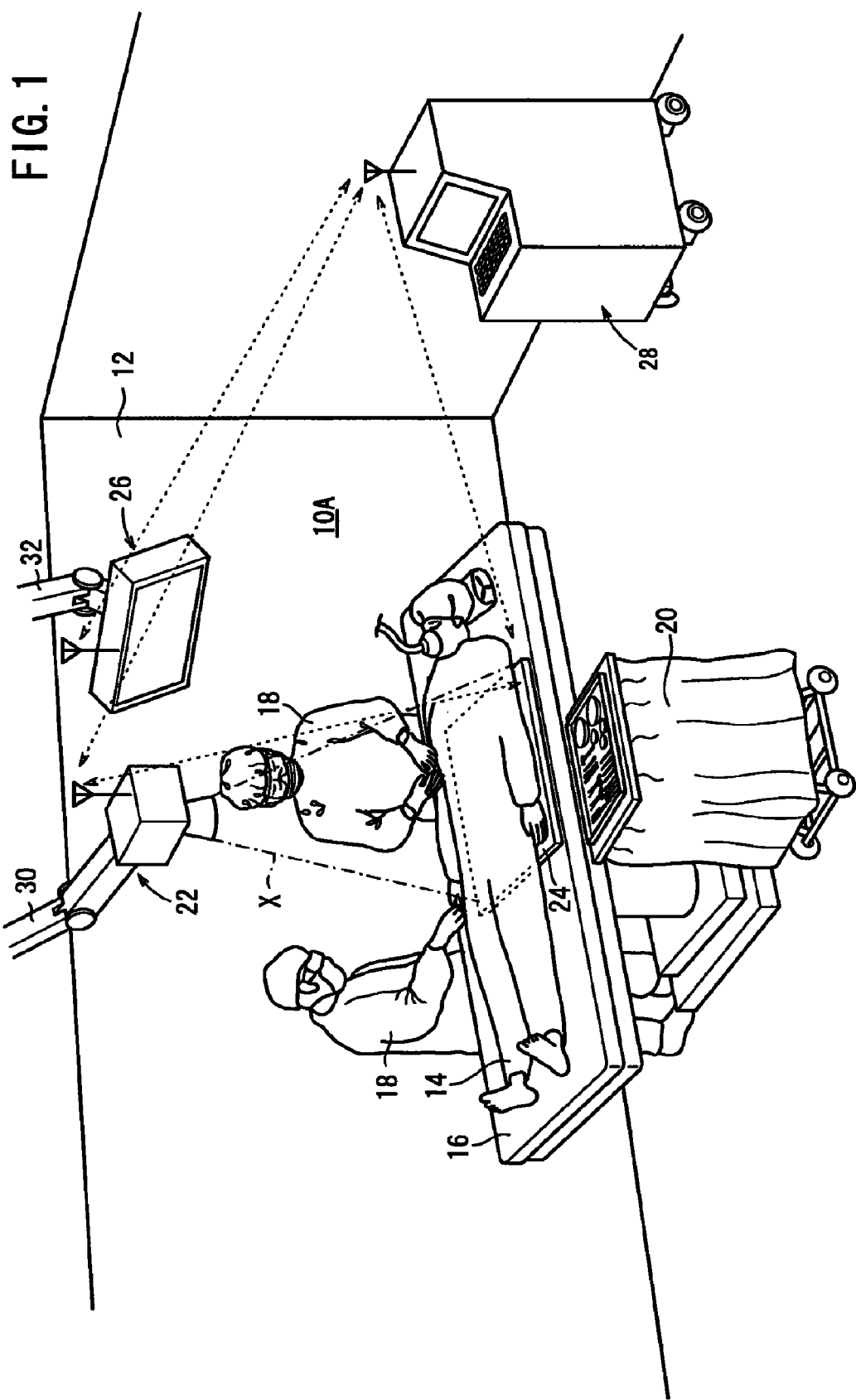
FIG. 1 is a perspective view of an operating room incorporating a radiographic image capturing system therein according to a first embodiment of the present invention.

As shown in FIG. 1, an operating room 12 houses therein the radiographic image capturing system 10A according to a first embodiment. The operating room 12 houses, in addition to the radiographic image capturing system 10, a surgical table (bed) 16 for a patient 14 to lie on, and an instrument table 20 disposed on one side of the surgical table 16 on which various tools and instruments are placed to be used by a surgeon 18 for operating on the patient 14. The surgical table 16 is surrounded by various apparatus required for surgical operations, including an anesthesia apparatus, an aspirator, an electrocardiograph, a blood pressure monitor, etc.

The radiographic image capturing system 10A includes an image capturing apparatus 22 for irradiating the patient 14 as a subject with radiation X at a dose according to image capturing conditions, a radiation detecting cassette 24 housing therein a radiation detector 40 (see FIGS. 2 through 4) for detecting radiation X that has passed through the patient 14, a display device 26 for displaying a radiographic image based on the radiation X, which is detected by the radiation detector 40, and a console (control device) 28 for generally controlling the image capturing apparatus 22, the radiation detecting cassette 24, and the display device 26. The image capturing apparatus 22, the radiation detecting cassette 24, the display device 26, and the console 28 send and receive signals by way of UWB (Ultra Wide Band) wireless communications.

The image capturing apparatus 22 is coupled to a universal arm 30 so as to be movable to a desired position depending on a desired area to be imaged of the patient 14, while also being retractable to a position out of the way of the surgeon 18 when the surgeon 18 performs a surgical operation on the patient 14. Similarly, the display device 26 is coupled to a universal arm 32 so as to be movable to a position where the surgeon 18 can easily confirm the captured radiographic images. The display device 26 may alternatively be fixed to the ceiling, a wall, or to the floor.

Figure 2:
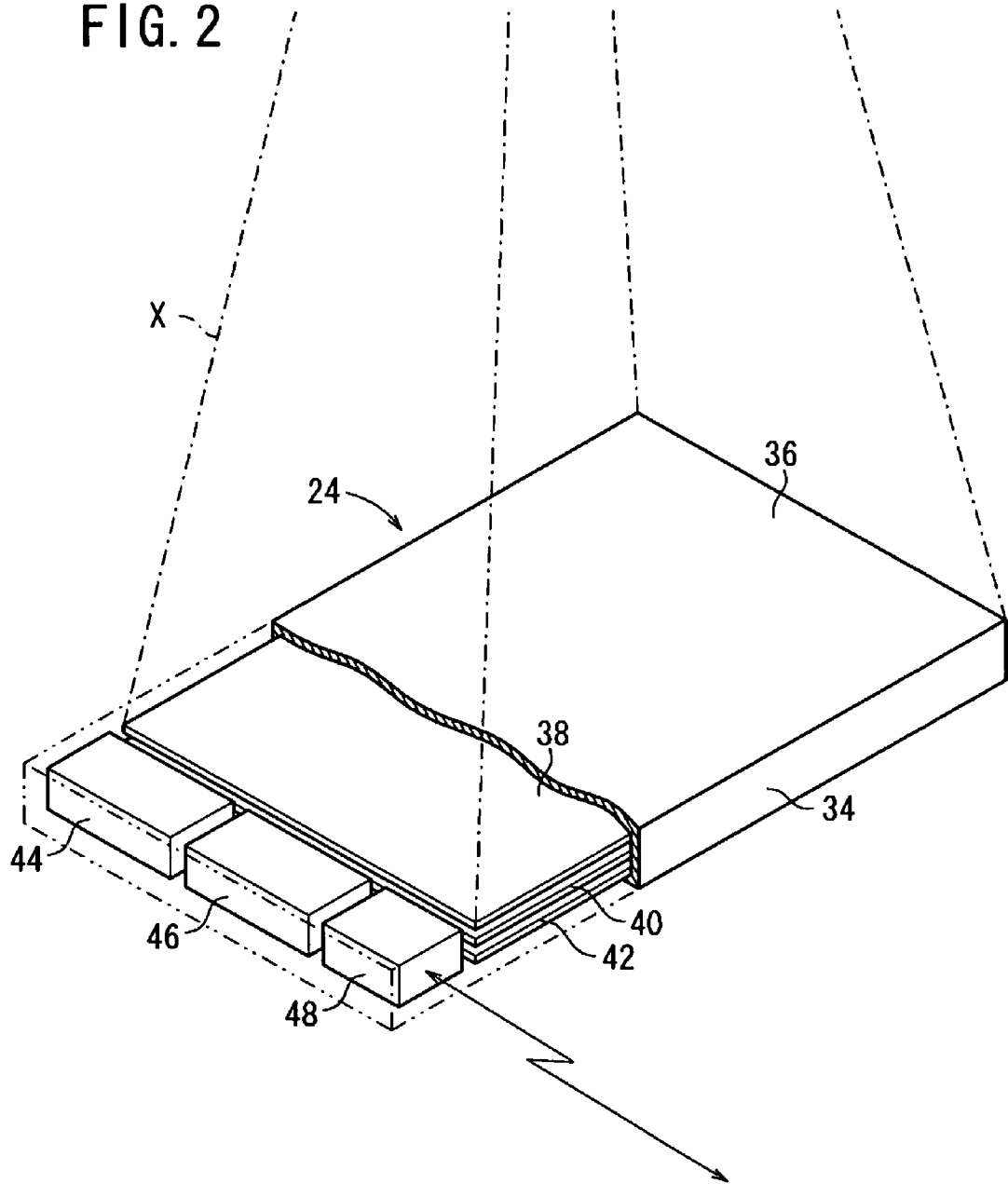
FIG. 2 is a perspective view, partially cut away, of a radiation detecting cassette shown in FIG. 1.

FIG. 2 is a perspective view, partially cut away, of the radiation detecting cassette 24 shown in FIG. 1. The radiation detecting cassette 24 has a box-shaped casing 34 made of a material permeable to radiation X. The casing 34 houses therein a grid 38 for removing scattered rays of radiation X from the patient 14, a radiation detector (radiation conversion panel) 40 for detecting radiation X that has passed through the patient 14, and a lead plate 42 for absorbing back scattered rays of radiation X, which are successively arranged in this order from an irradiated surface 36 of the casing 34, which is irradiated with the radiation X. The irradiated surface 36 of the casing 34 may be constructed as the grid 38.

The casing 34 also houses therein a power supply 44 including a battery for energizing the radiation detecting cassette 24, a cassette controller 46 for energizing the radiation detector 40 with electric power supplied from the power supply 44, and a transceiver (wireless communicating means) 48 for sending and receiving signals, including information of the radiation X detected by the radiation detector 40, to and from the console 28. A lead plate or the like preferably should be placed over side surfaces of the cassette controller 46 and the transceiver 48, which is disposed under the irradiated surface 36 of the casing 34, in order to protect the cassette controller 46 and the transceiver 48 against damage, which would otherwise be caused if the cassette controller 46 and the transceiver 48 were irradiated with radiation X.

Figure 3:
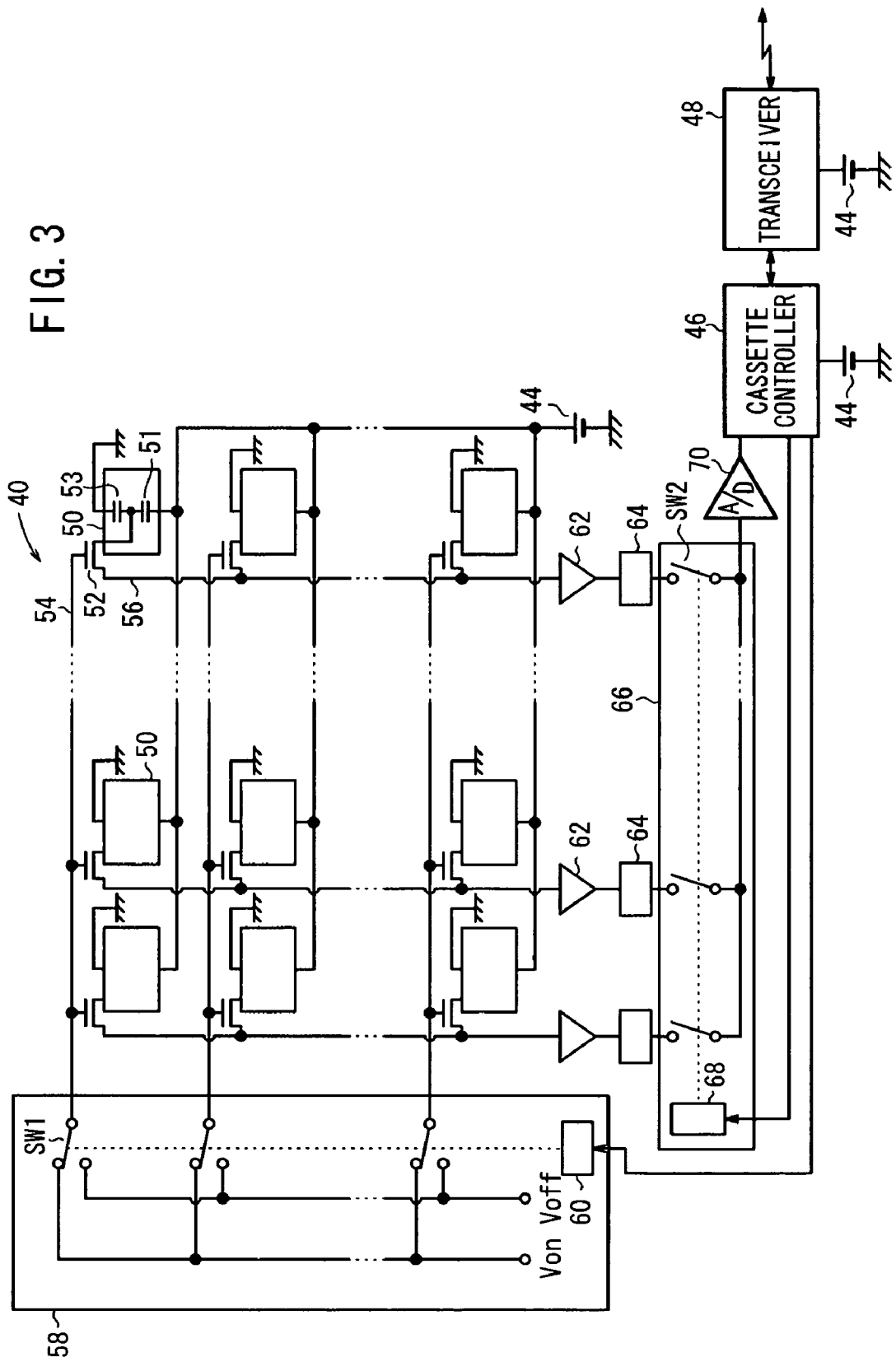
FIG. 3 is a block diagram of a circuit arrangement of a radiation detector shown in FIG. 2.

FIG. 3 shows in block form a circuit arrangement for the radiation detector 40. The radiation detector 40 comprises an array of thin-film transistors (TFTs) 52 arranged in rows and columns, a photoelectric conversion layer 51 made of a material such as amorphous selenium (a-Se) for generating electric charges upon detection of radiation X, the photoelectric conversion layer 51 being disposed on the array of TFTs 52, and an array of storage capacitors 53 connected to the photoelectric conversion layer 51. When radiation X is applied to the radiation detector 40, the photoelectric conversion layer 51 generates electric charges, and the storage capacitors 53 store the generated electric charges. Then, the TFTs 52 are turned on, each row at a time, in order to read the electric charges from the storage capacitors 53 as an image signal. In FIG. 3, the photoelectric conversion layer 51 and one of the storage capacitors 53 are shown as representing a pixel 50, with the pixel 50 being connected to one of the TFTs 52. Details of the other pixels 50 have been omitted from illustration. Since amorphous selenium tends to change in structure and lose the functions thereof at high temperatures, amorphous selenium needs to be used within a certain temperature range. Therefore, some means for cooling the radiation detector 40 should preferably be provided in the cassette 24.

The TFTs 52 connected to the respective pixels 50 are connected to respective gate lines 54 that extend in parallel to the rows, and to respective signal lines 56 that extend in parallel to the columns. The gate lines 54 are connected to a line scanning driver 58, and the signal lines 56 are connected to a multiplexer 66, which serves as a reading circuit. The gate lines 54 are supplied with control signals Von, Voff from the line scanning driver 58 for turning on and off the TFTs 52 along the rows. The line scanning driver 58 comprises a plurality of switches SW1 for switching between the gate lines 54, and an address decoder 60 for outputting a selection signal for selecting one of the switches SW1 at a time. The address decoder 60 is supplied with address signals from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56, and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiographic image signal generated by the multiplexer 66 based on the electric charges from the sample and hold circuits 64 is converted by the A/D converter 70 into digital image signals representing the radiographic image information, which is supplied to the cassette controller 46.

Figure 4:
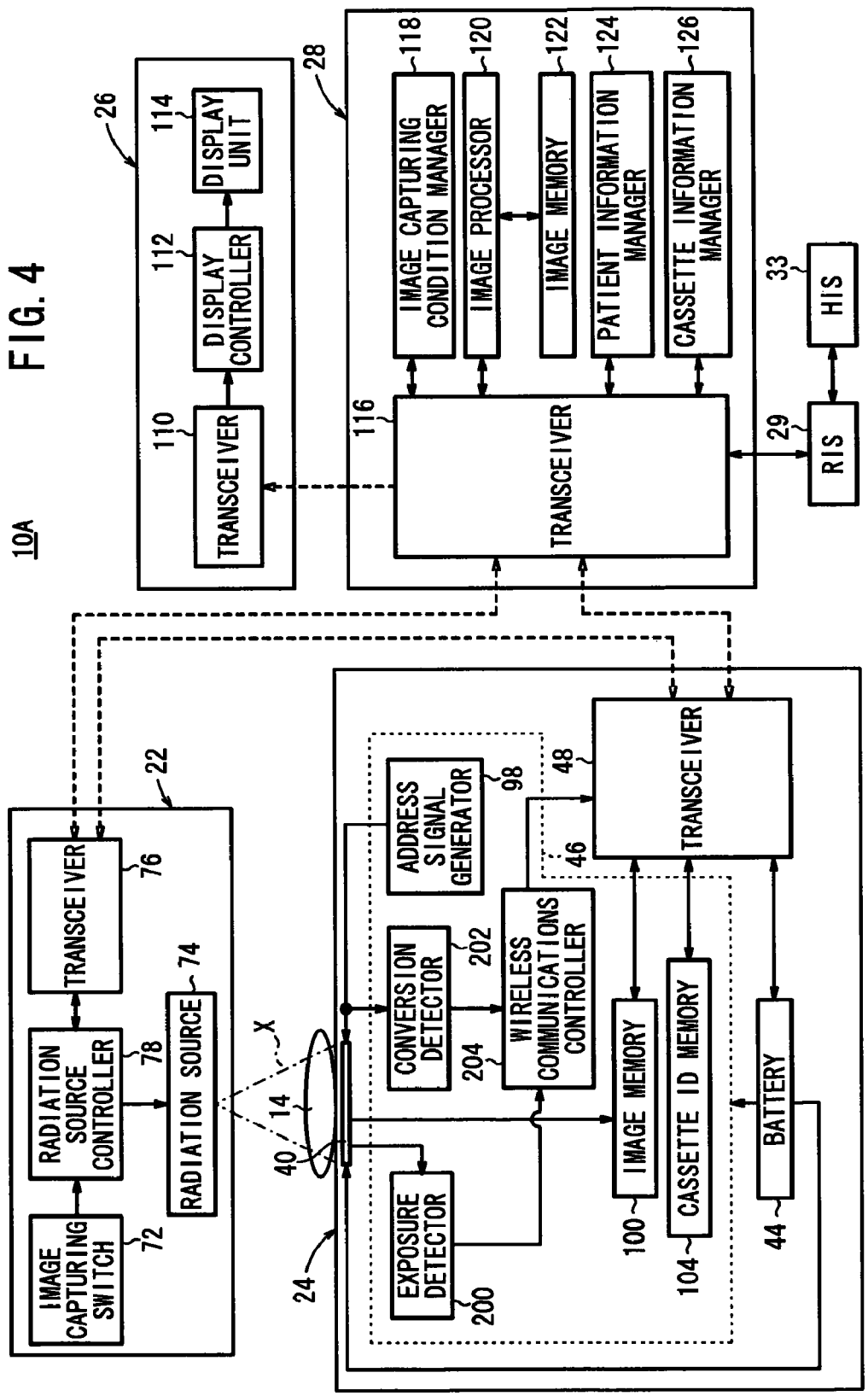
FIG. 4 is a block diagram of the radiographic image capturing system shown in FIG. 1.

FIG. 4 shows in block form the radiographic image capturing system 10A, which comprises the image capturing apparatus 22, the radiation detecting cassette 24, the display device 26, and the console 28. The console 28 is connected to a radiology information system (RIS, information management system) 29, which stores and generally manages radiographic image information handled by the radiological department of the hospital, along with other information. The RIS 29 is connected to a hospital information system (HIS) 33, which generally manages medical information in the hospital.

The image capturing apparatus 22 comprises an image capturing switch 72, a radiation source 74, a transceiver (wireless communicating means) 76, and a radiation source controller 78.

The transceiver 76 receives image capturing conditions from the console 28 by way of wireless communications, and transmits an image capturing completion signal, etc., to the console 28 by way of wireless communications. The transceiver 76 also is capable of wireless communications with the transceiver 48 of the radiation detecting cassette 24.

The radiation source controller 78 controls the radiation source 74 based on an image capturing start signal supplied from the image capturing switch 72 and image capturing conditions supplied from the transceiver 76. The radiation source 74 outputs radiation X under the control of the radiation source controller 78.

The cassette controller 46 of the radiation detecting cassette 24 comprises an address signal generator (address signal generating means) 98, an image memory 100, a cassette ID memory 104, an exposure detector (exposure detecting means) 200, a conversion detector (conversion detecting means) 202, and a wireless communications controller (wireless communications controlling means) 204.

The address signal generator 98 supplies address signals to the address decoder 60 of the line scanning driver 58 and the address decoder 68 of the multiplexer 66 of the radiation detector 40. The image memory 100 stores radiographic image information detected by the radiation detector 40. The cassette ID memory 104 stores cassette ID information for identifying the radiation detecting cassette 24.

The transceiver 48 receives a transmission request signal from the console 28 by way of wireless communications, and transmits the cassette ID information stored in the cassette ID memory 104 along with the radiographic image information stored in the image memory 100 to the console 28 by way of wireless communications. The power supply 44 of the radiation detecting cassette 24 may be supplied with electric power from an external circuit, such as the console 28 or the like, via the transceiver 48 by way of wireless communications.

The exposure detector 200 specifies a given pixel 50, which is located in an area where the patient 14 is less likely to be placed between the radiation source 74 and the radiation detecting cassette 24, and then detects application (exposure) of radiation X to the radiation detector 40 based on the dose of radiation X that is detected by the specified pixel 50, whereupon the exposure detector 200 outputs the detected result as an exposure detection signal to the wireless communications controller 204.

The conversion detector 202 detects the supply of address signals from the address signal generator 98 to the address decoders 60, 68, and outputs the detected result as a conversion detection signal to the wireless communications controller 204. Since the radiation detector 40 converts the detected radiation X into radiographic image information based on the supply of address signals from the address signal generator 98 to the address decoders 60, 68, the conversion detection signal serves as a signal which is indicative of conversion of the detected radiation X into radiographic image information by the radiation detector 40.

When the wireless communications controller 204 is supplied either with the exposure detection signal from the exposure detector 200 or with the conversion detection signal from the conversion detector 202, the wireless communications controller 204 controls the transceiver 48 so as to inhibit wireless communications with external circuits. Therefore, within a time zone during which the exposure detection signal is supplied from the exposure detector 200 to the wireless communications controller 204, or within a time zone during which the conversion detection signal is supplied from the conversion detector 202 to the wireless communications controller 204, the transceiver 48 is incapable of sending signals, e.g., radiographic image information, to the console 28 by way of wireless communications, and the transceiver 48 also is incapable of supplying electric power from an external circuit to the power supply 44 by way of wireless communications. In other words, the wireless communications controller 204 controls the transceiver 48 so as not to perform wireless communications within the same time zone at which radiation X is applied to the radiation detector 40, and during which radiation X is converted into radiographic image information by the radiation detector 40.

The display device 26 comprises a receiver 110 for receiving radiographic image information from the console 28, a display controller 112 for controlling the display of received radiographic image information, and a display unit 114 for displaying the radiographic image information processed by the display controller 112.

The console 28 comprises a transceiver 116, an image capturing condition manager 118, an image processor (image processing means) 120, an image memory 122, a patient information manager 124, and a cassette information manager 126.

The transceiver 116 transmits and receives essential information including radiographic image information to and from the image capturing apparatus 22, the electronic cassette 24, and the display device 26 by way of wireless communications. The image capturing condition manager 118 manages image capturing conditions required in order for the image capturing apparatus 22 to capture radiographic images. The image processor 120 processes radiographic image information transmitted from the radiation detecting cassette 24. The image memory 122 stores the radiographic image information processed by the image processor 120. The patient information manager 124 manages patient information of a patient 14 whose images are to be captured. The cassette information manager 126 manages the cassette ID information transmitted from the radiation detecting cassette 24.

The console 28 may be located outside of the operating room 12, insofar as the console 28 can transmit and receive signals to and from the image capturing apparatus 22, the radiation detecting cassette 24, and the display device 26 by way of wireless communications.

The image capturing conditions refer to conditions for determining a tube voltage, a tube current, an irradiation time, etc., which are required to apply radiation X at an appropriate dose to an area to be imaged of the patient 14. The image capturing conditions may include an area to be imaged of the patient 14, an image capturing method, etc., for example. The patient information refers to information for identifying the patient 14, such as the name, gender, patient ID number, etc., of the patient 14. Command information for instructing the radiographic image capturing system 10A to capture a radiation image, including the image capturing conditions and the patient information, can be set directly using the console 28, or can be supplied from an external circuit to the console 28 via the RIS 29.

The radiographic image capturing system 10A according to the first embodiment basically is constructed as described above. Operations of the radiographic image capturing system 10A will be described below.

The radiographic image capturing system 10A is installed in an operating room 12 and is used when radiographic images of the patient 14 are required by a surgeon 18 performing a surgical operation on the patient 14. Before radiographic images of the patient 14 are captured, patient information of the patient 14 to be imaged is registered in advance in the patient information manager 124 of the console 28. If an area to be imaged of the patient 14 and an image capturing method are known beforehand, such items are registered in advance as image capturing conditions in the image capturing condition manager 118. After the above preparatory process is finished, the surgeon 18 performs a surgical operation on the patient 14.

For capturing radiographic images of the patient 14 during the surgical operation, the surgeon 18 or a radiological technician operating the radiographic image capturing system 10A places the radiation detecting cassette 24 in a desired position between the patient 14 and the surgical table 16, with the irradiated surface 36 facing toward the image capturing apparatus 22. Then, the surgeon 18 or the radiological technician moves the image capturing apparatus 22 to a position facing the radiation detecting cassette 24, and then turns on the image capturing switch 72 in order to capture a radiation image of the patient 14.

When the image capturing switch 72 is turned on, the radiation source controller 78 of the image capturing apparatus 22 sends a request to the console 28 for sending the image capturing conditions via the transceivers 76, 116. Based on the received request, the console 28 sends the image capturing conditions for an area to be imaged of the patient 14, which are registered in the image capturing condition manager 118, to the image capturing apparatus 22 via the transceivers 116, 76. When the radiation source controller 78 receives the image capturing conditions, the radiation source controller 78 controls the radiation source 74 in order to apply radiation X at a given dose to the patient 14 according to the image capturing conditions.

Radiation X that has passed through the patient 14 is applied to the grid 38, which removes scattered rays from the radiation X. Then, the radiation X is applied to the radiation detector 40, and converted into electric signals by the photoelectric conversion layer 51 including the pixels 50 of the radiation detector 40. The electric signals are stored as electric charges in the storage capacitors 53 (see FIG. 3). The stored electric charges, which represent radiographic image information of the patient 14, are read from the storage capacitors 53 according to address signals, which are supplied from the address signal generator 98 of the cassette controller 46 to the line scanning driver 58 and the multiplexer 66.

More specifically, in response to the address signal supplied from the address signal generator 98, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 98, the address decoder 68 of the multiplexer 66 outputs selection signals to successively turn on the switches SW2 to switch between the signal lines 56, for thereby reading through the signal lines 56 the electric charges stored in the storage capacitors 53 of the pixels 50 connected to the selected gate line 54.

The electric charges read from the storage capacitors 53 of the pixels 50 connected to the selected gate line 54 are amplified by respective amplifiers 62, sampled by the sample and hold circuits 64, and supplied to the multiplexer 66. Based on the supplied electric charges, the multiplexer 66 generates and supplies a radiographic image signal to the A/D converter 70, which converts the radiographic image signal into digital signals. Such digital signals, which represent the radiographic image information, are stored in the image memory 100 of the cassette controller 46.

Similarly, the address decoder 60 of the line scanning driver 58 successively turns on the switches SW1 to switch between the gate lines 54 according to the address signal supplied from the address signal generator 98. The electric charges stored in the storage capacitors 53 of the pixels 50 connected to the successively selected gate lines 54 are read through the signal lines 56, and processed by the multiplexer 66 and the A/D converter 70 into digital signals, which are stored in the image memory 100 of the cassette controller 46.

The exposure detector 200 outputs an exposure detection signal to the wireless communications controller 204 based on the dose of radiation X detected by the specific pixel 50, which is located in an area where the patient 14 is less likely to be placed between the radiation source 74 and the radiation detecting cassette 24, and only within a time zone during which radiation X is applied to the radiation detector 40. The conversion detector 202 outputs a conversion detection signal to the wireless communications controller 204 only within a time zone during which the address signals are supplied from the address signal generator 98 to the address decoders 60, 68. The wireless communications controller 204 controls the transceiver 48 to inhibit wireless communications with external circuits, when it is supplied with the exposure detection signal from the exposure detector 200, or when it is supplied with the conversion detection signal from the conversion detector 202. However, the wireless communications controller 204 permits the transceiver 48 to perform wireless communications with external circuits during times when it is not supplied with the exposure detection signal or the conversion detection signal.

Therefore, the radiographic image information stored in the image memory 100 is transmitted to the console 28 via the transceiver 48 by way of wireless communications within a time zone during which the transceiver 48 is permitted by the wireless communications controller 204 to perform wireless communications, i.e., within a time zone during which radiation X is not being applied to the radiation detector 40, and during which conversion into radiographic image information is not being carried out by the radiation detector 40.

The radiographic image information transmitted to the console 28 is received by the transceiver 116, processed by the image processor 120, and then stored in the image memory 122 in association with patient information of the patient 14, which is registered in the patient information manager 124.

The processed radiographic image information is transmitted from the transceiver 116 to the display device 26. In the display device 26, the receiver 110 receives the radiographic image information, and the display controller 112 controls the display unit 114 to display a radiographic image based on the radiation image information. The surgeon 18 therefore performs a surgical operation on the patient 14 while visually confirming the radiographic image displayed on the display unit 114.

Similar to the above-described transmission of radiographic image information by way of wireless communications, supply of electric power from an external circuit (e.g., the console 28) to the power supply 44 by way of wireless communications is performed within a time zone during which the transceiver 48 is permitted to perform wireless communications.

With the radiographic image capturing system 10A according to the first embodiment, the wireless communications controller 204 of the radiation detecting cassette 24 controls the transceiver 48 in order to inhibit transmission of radiographic image information to an external circuit by way of wireless communications, and also to inhibit the supply of electric power from an external circuit to the power supply 44 by way of wireless communications, based on the exposure detection signal from the exposure detector 200 and the conversion detection signal from the conversion detector 202.

Consequently, the transceiver 48 can be controlled so as not to carry out application of radiation X to the radiation detector 40, as well as not to perform conversion into radiographic image information by the radiation detector 40, within the same time zone as wireless communications by the transceiver 48. As a result, electromagnetic noise caused by the application of radiation X and electromagnetic noise caused by address signals, control signals Von, Voff, and selection signals, which are used by the radiation detector 40 to perform conversion, are reliably prevented from being added to the radiographic image information transmitted to an external circuit by way of wireless communications, and to the electric power supplied from an external circuit to the power supply 44 by way of wireless communications. Accordingly, the adverse effect that the electromagnetic noises could have on the radiographic image information and the electric power transmitted by way of wireless communications can reliably be removed.

Electromagnetic noise, which is caused by address signals, control signals Von, Voff, and selection signals that are used by the radiation detector 40 to perform conversion, includes electromagnetic noise caused by magnetic fields, which are generated when an address signal is supplied to an address signal supply line, electromagnetic noise caused by a magnetic fields, which are generated when the control signals Von, Voff are supplied to the gate lines 54, and electromagnetic noise caused by a magnetic fields, which are generated when selection signals are supplied to the selection signal supply lines.

With the radiographic image capturing system 10A according to the first embodiment, the transceiver 48 is controlled so as not to carry out application of radiation X to the radiation detector 40, as well as not to perform conversion into radiographic image information by the radiation detector 40, within the same time zone during which wireless communications are conducted by the transceiver 48. Instead, the transceiver 48 may be controlled so as not to perform either application of radiation X to the radiation detector 40, or conversion into radiographic image information by the radiation detector 40, within the same time zone during which wireless communications are performed by the transceiver 48.

With the radiographic image capturing system 10A according to the first embodiment, furthermore, the transceiver 48 is controlled so as not to perform application of radiation X to the radiation detector 40, and not to carry out conversion into radiographic image information by the radiation detector 40, within the same time zone during which transmission of radiographic image information to an external supply by way of wireless communications, and supply of electric power from an external circuit to the power supply 44 by way of wireless communications, are carried out. Instead, the transceiver 48 may be controlled so as not to perform application of radiation X to the radiation detector 40, and not to perform conversion into radiographic image information by the radiation detector 40, within the same time zone during which either transmission of radiographic image information to an external supply by way of wireless communications, or supply of electric power from an external circuit to the power supply 44 by way of wireless communications, is being carried out.

Furthermore, signals are transmitted and received by way of UWB wireless communications between the radiation detecting cassette 24 and the console 28, between the radiation detecting cassette 24 and the image capturing apparatus 22, between the image capturing apparatus 22 and the console 28, and between the console 28 and the display device 26. In other words, since cables for transmitting and receiving signals are not connected between the image capturing apparatus 22, the radiation detecting cassette 24, the display device 26, and the console 28, no cables are placed on the floor of the operating room 12, and thus no obstacles are presented to operations performed by the surgeon 18, the radiological technician, or other staff members working in the operating room 12. The surgeon 18 in the operating room 12 can thus work efficiently. UWB wireless communications make it possible to reduce power consumption, increase fading resistance, and increase communication rates, compared with other wireless communications according to the background art.

The radiographic image capturing system 10A according to the first embodiment is not limited to the features described above, but may be freely modified to include other various arrangements.

More specifically, the radiographic image capturing system 10A according to the first embodiment captures a radiographic image of the patient 14 when the surgeon 18 or the radiological technician turns on the image capturing switch 72. However, the system may capture a radiographic image of the patient 14 when a surgeon 18 or the radiological technician performs an operation through the console 28.

In the radiographic image capturing system 10A according to the first embodiment, radiographic images used in a surgical operation are displayed by the display device 26. However, the radiographic image capturing system 10A may be used to capture ordinary radiographic images, in applications other than surgical operations.

In the radiographic image capturing system 10A according to the first embodiment, the radiation detector 40 housed in the radiation detecting cassette 24 directly converts the dose of applied radiation X into electric signals using the photoelectric conversion layer 51. However, the radiographic image capturing system 10A may employ a radiation detector, which includes a scintillator for converting applied radiation X into visible light, and a solid-state detecting device made up of amorphous silicon (a-Si) or the like, for converting the visible light into electric signals (see Japanese Patent No. 3494683).

Alternatively, the radiographic image capturing system 10A may employ a light-conversion radiation detector for acquiring radiation image information. Such a light-conversion radiation detector operates as follows: When radiation is applied to a matrix of solid-state detecting devices, the solid-state detecting devices store an electrostatic latent image, which depends on the dose of applied radiation. For reading the stored electrostatic latent image, reading light is applied to the solid-state detecting devices, in order to cause the solid-state detecting devices to generate electric currents representing radiation image information. Further, when erasing light is applied to the radiation detector, radiation image information representing a residual electrostatic latent image is erased from the radiation detector, which can then be reused (see Japanese Laid-Open Patent Publication No. 2000-105297).

A radiographic image capturing system 10B according to a second embodiment will be described below with reference to FIGS. 5 through 8. Those components of the radiographic image capturing system 10B which are identical to components of the radiographic image capturing system 10A according to the first embodiment (FIGS. 1 through 4) shall be denoted by identical reference characters, and such features will not be described in detail below. This also holds true for the other embodiments.

Figure 5:
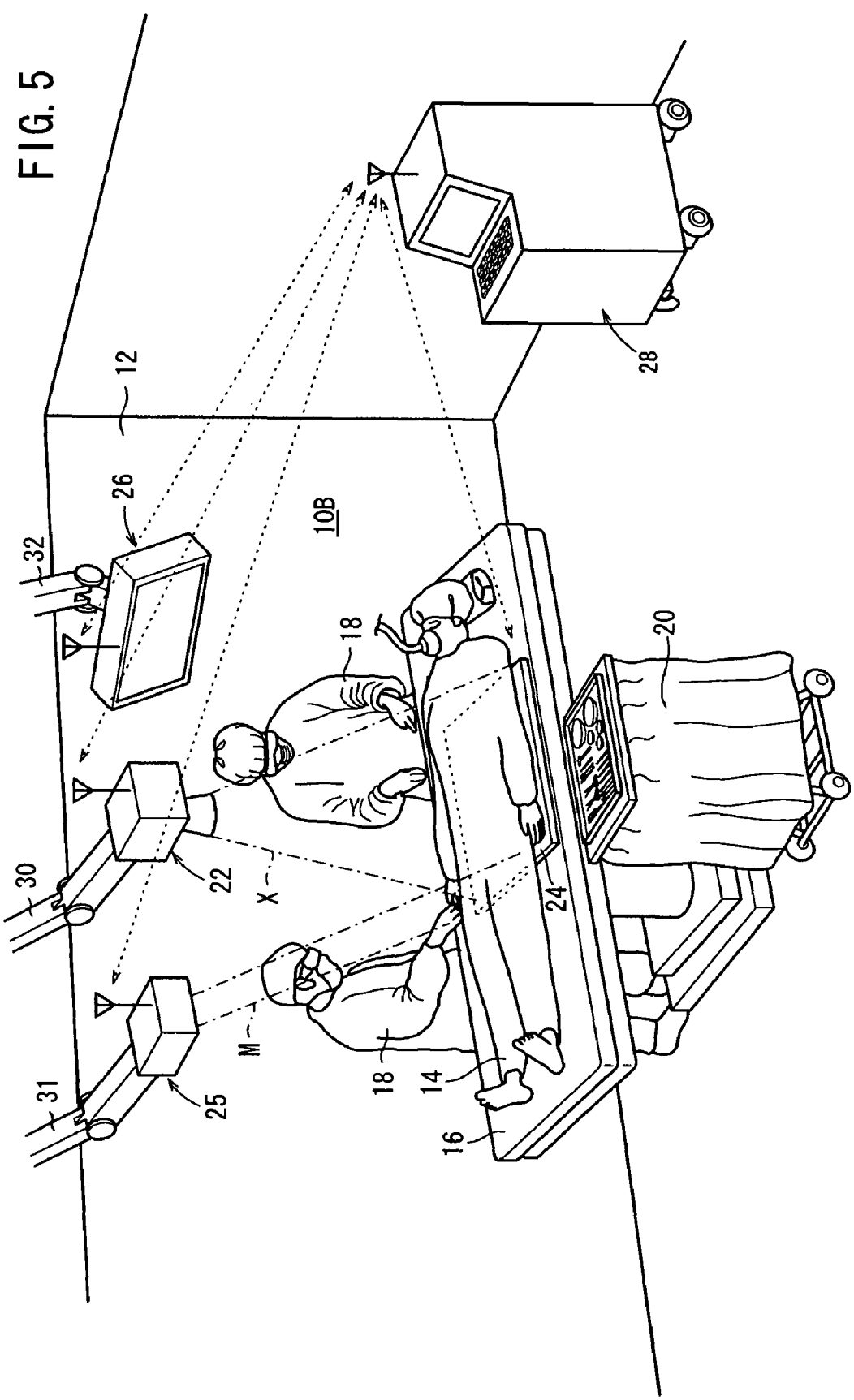
FIG. 5 is a perspective view of an operating room incorporating a radiographic image capturing system therein according to a second embodiment of the present invention.

As shown in FIG. 5, the radiographic image capturing system 10B according to the second embodiment includes a power feeder 25 for supplying electric power wirelessly (contactlessly) to the radiation detecting cassette 24. The image capturing apparatus 22, the radiation detecting cassette 24, the power feeder 25, the display device 26, and the console 28 send and receive signals by way of UWB wireless communications.

The power feeder 25 is coupled to a universal arm 31 that extends from the ceiling, so as to be movable to any desired position depending on the location of the radiation detecting cassette 24. The power feeder 25 may alternatively be fixed to the ceiling, a wall, or to the floor.

Figure 6:
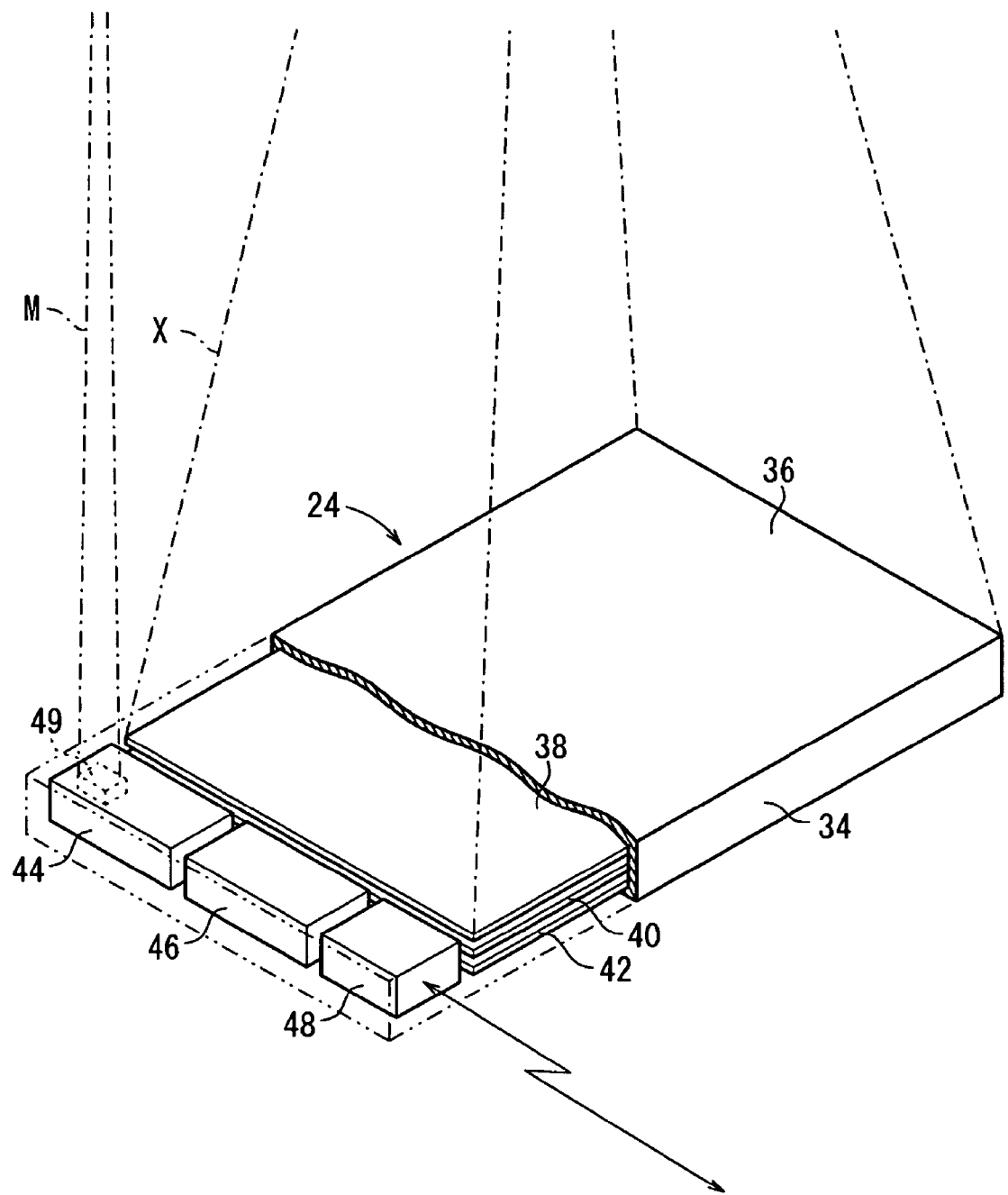
FIG. 6 is a perspective view, partially cut away, of a radiation detecting cassette shown in FIG. 5.

FIG. 6 is a perspective view, partially cut away, of the radiation detecting cassette 24 shown in FIG. 5. The power supply 44 includes an energy converter 49 (see FIG. 7) for converting a magnetic field M (energy, supplied energy) converted from electric energy and applied from the power feeder 25 back into electric energy.

Figure 7:
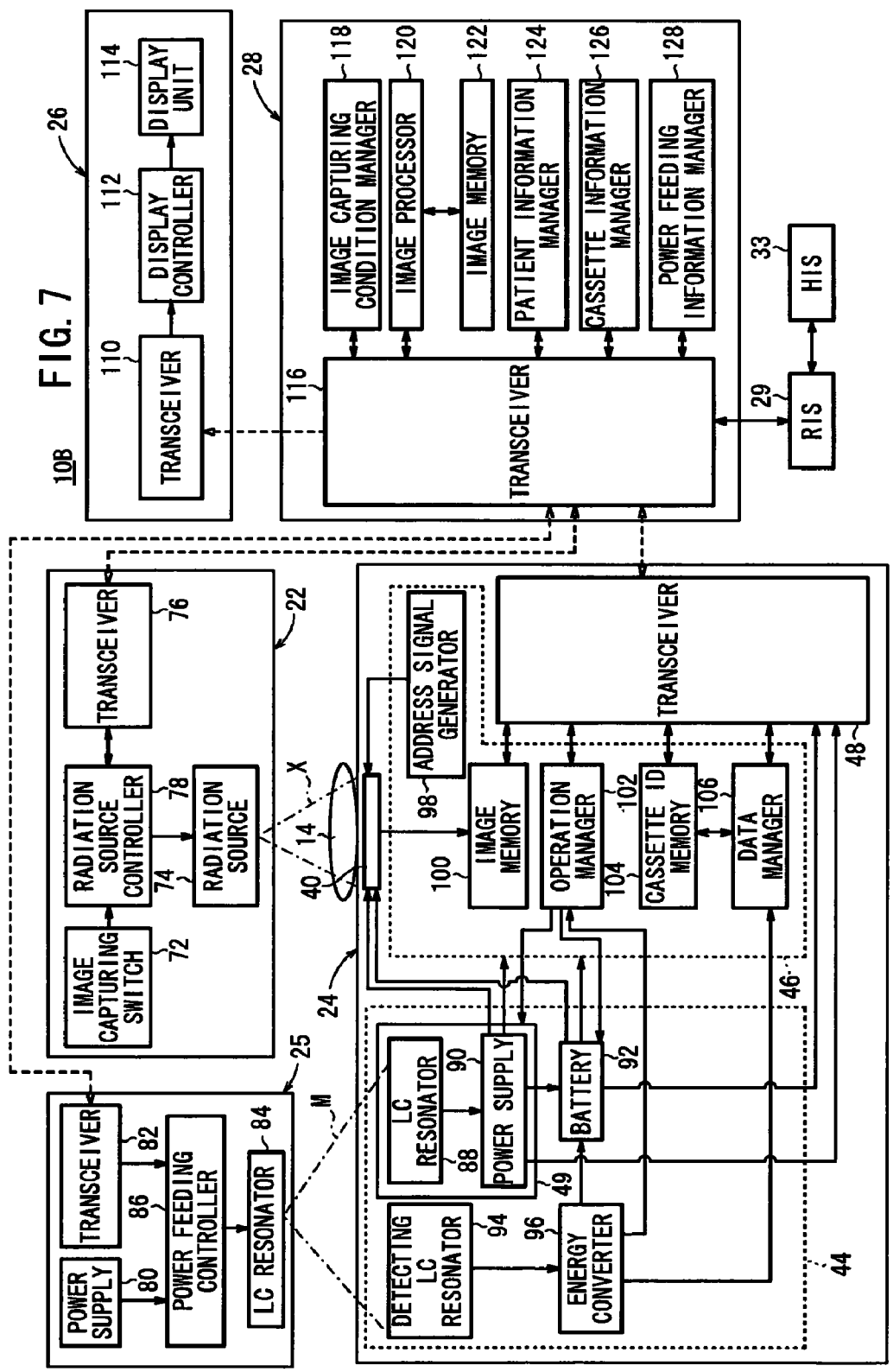
FIG. 7 is a block diagram of the radiographic image capturing system shown in FIG. 5.

FIG. 7 is a block diagram of the radiographic image capturing system 10B, which comprises the image capturing apparatus 22, the radiation detecting cassette 24, the power feeder 25, the display device 26, and the console 28.

The power feeder 25 comprises a power supply 80 connected to an external power source or the like, not shown, a transceiver 82 for receiving a power feeding start signal, etc., from the console 28 by way of wireless communications and sending ID information (identification data), etc., of the power feeder 25 to the console 28 by way of wireless communications, an LC resonator (electric power transmitting means) 84 for converting electric energy from the power supply 80 into a magnetic field M and wirelessly supplying the magnetic field M to the radiation detecting cassette 24, and a power feeding controller 86 for controlling the LC resonator 84 based on the power feeding start signal supplied from the transceiver 82.

The power supply 44 of the radiation detecting cassette 24 includes an energy converter 49, which has an LC resonator 88 for receiving the magnetic field M applied from the LC resonator 84 of the power feeder 25 and converting the magnetic field M back into electric energy, and a power supply 90 for supplying the electric energy converted by the LC resonator 88 as desired electric power to the radiation detector 40, the cassette controller 46, the transceiver 48, and a battery 92 chargeable by the power supply 90. The power supply 44 also includes a detecting LC resonator 94 disposed in parallel with the LC resonator 88 and which is smaller in size than the LC resonator 88, and an energy detector (electric power reception on/off detector) 96 for detecting that the radiation detecting cassette 24 has been positioned within a feeding area of the power feeder 25 by detecting the electric energy converted back by the detecting LC resonator 94, and sending a feeding area detection signal to the cassette controller 46. The power feeder 25 thus wirelessly supplies electric power to the radiation detecting cassette 24 according to a known power transmission technique, which utilizes the resonance of the magnetic field M from the LC resonator 84 to the LC resonator 88.

The cassette controller 46 has, in addition to the address signal generator 98, the image memory 100 and the cassette ID memory 104, an operation manager 102 for controlling the power supply 44 so as to control energization of the radiation detecting cassette 24, and a data manager 106 for managing ID information (identification data) for identifying the power feeder 25, which feeds power to the radiation detecting cassette 24, and a feeding area detection signal from the energy detector 96. The radiographic image capturing system 10B according to the second embodiment also differs from the radiographic image capturing system 10A according to the first embodiment (FIGS. 1 through 4), in that the cassette controller 46 does not contain the exposure detector 200, the conversion detector 202, and the wireless communications controller 204 (see FIGS. 4 and 7).

The transceiver 48 receives a transmission request signal and the ID information of the power feeder 25 from the console 28 by way of wireless communications, and transmits to the console 28 by way of wireless communications the radiographic image information stored in the image memory 100, the cassette ID information stored in the cassette ID memory 104, and a wireless feeding enable signal from the data manager 106 based on the feeding area detection signal from the energy detector 96.

The console 28 includes a power feeding information manager 128 for managing ID information, etc., transmitted from the power feeder 25, in addition to the transceiver 116, the image capturing condition manager 118, the image processor 120, the image memory 122, the patient information manager 124, and the cassette information manager 126 for managing cassette information including the wireless feeding enable signal sent from the radiation detecting cassette 24. The cassette information includes the wireless feeding enable signal from the data manager 106, in addition to the cassette ID information for identifying the radiation detecting cassette 24.

The radiographic image capturing system 10B according to the second embodiment basically is constructed as described above. Operations of the radiographic image capturing system 10B will be described below.

For capturing radiographic images of the patient 14 during a surgical operation, the surgeon 18 or the radiological technician places the radiation detecting cassette 24 in a desired position between the patient 14 and the surgical table 16, with the irradiated surface 36 facing toward the image capturing apparatus 22. At the same time that the console 28 starts to operate, or when the surgeon 18 or the radiological technician turns on an operation start switch, not shown, the power feeder 25 is energized under given operating conditions (i.e., a low output operation mode). At this time, the radiation detecting cassette 24 is detected as being placed in the feeding area of the power feeder 25 by the detecting LC resonator 94 and the energy detector 96 of the power supply 44. More specifically, the energy detector 96 functions as a power feeding on/off detector for detecting whether or not the radiation detecting cassette 24 has been placed in the feeding area of the power feeder 25. At this time, the power feeding controller 86 of the power feeder 25 operates in a low output operation mode for applying a relatively weak magnetic field M from the LS resonator 84, which can be detected by the detecting LC resonator 94 and the energy detector 96 of the radiation detecting cassette 24. Therefore, power consumption of the power feeder 25 is kept at a low level.

In the radiation detecting cassette 24, the energy detector 96 supplies a feeding area detection signal to the data manager 106. In response to the feeding area detection signal, the data manager 106 receives the ID information of the power feeder 25, which is stored in the power feeding information manager 128 of the console 28, via the transceivers 82, 116, and transmits the wireless feeding enable signal to the cassette information manager 126 via the transceivers 48, 116. Since the power feeding start signal is sent from the cassette information manager 126 to the power feeder 25 via the transceivers 116, 82, the power feeding controller 86 controls the LC resonator 84 in order to start feeding power to the radiation detecting cassette 24. Specifically, the power feeder 25 is energized to apply the magnetic field M from the LC resonator 84 to the radiation detecting cassette 24, under operating conditions for a stronger level (i.e., high output operation mode, power feeding operation mode). In the radiation detecting cassette 24, the magnetic field M from the LC resonator 84 is converted into electric energy by the LC resonator 88, and the electric energy is supplied to the power supply 90 based on a control command from the operation manager (controller) 102 to the energy converter 49. The power supply 90 starts to supply electric power to the radiation detector 40, etc., thereby completing preparations for image capturing.

The radiographic image capturing system 10B allows the console 28 to confirm the ID information of the power feeder 25 that is associated with the radiation detecting cassette 24. Accordingly, even if the radiographic image capturing system 10B includes a plurality of power feeders that are usable selectively, the radiation detecting cassette 24 can be supplied with electric power from a desired and selected one of the power feeders. As a result, wasteful power consumption and erroneous operations can be avoided.

Then, the image capturing apparatus 22 is moved to a position facing the radiation detecting cassette 24, after which the image capturing switch 72 is operated in order to capture a radiographic image, in the same manner as the radiographic image capturing system 10A according to the first embodiment (FIGS. 1 through 4).

As described above, the radiographic image capturing system 10B according to the second embodiment includes the power feeder 25 disposed in a position capable of wirelessly feeding power to the radiation detecting cassette 24 at all times when the radiation detecting cassette 24 is used (while radiographic images are captured). Therefore, the radiographic image capturing system 10B according to the second embodiment offers advantages, in addition to the advantages of the above radiographic image capturing system 10A according to the first embodiment (FIGS. 1 through 4), in that the radiographic image capturing system 10B can capture radiographic images without requiring power cables to be connected to the radiation detecting cassette 24. Thus, not only the radiation detecting cassette 24, but also the system as a whole, can be handled with ease. Furthermore, the process of capturing radiographic images and surgical operations are effectively prevented from becoming interrupted due to an excessively low remaining power level in the battery of the radiation detecting cassette 24.

With the radiographic image capturing system 10B, when the radiation detecting cassette 24 is placed in the feeding area of the power feeder 25, the radiation detecting cassette 24 and the power feeder 25 automatically exchange information with each other through the console 28, and the radiation detecting cassette 24 is brought into a state capable of capturing a radiographic image. Consequently, the radiation detecting cassette 24 does not need to be activated and placed in a preparatory state for capturing radiographic images, using the battery 92, etc., and the radiation detecting cassette 24 does not require a manual power supply switch. Wasteful power consumption and malfunctioning is avoided, and the surgeon 18 or the radiological technician can be prevented from making a mistake, such as not capturing a radiographic image by forgetting to operate a manual power supply switch. Accordingly, the radiographic image capturing system 10B including the radiation detecting cassette 24 can be handled with greater ease.

Since the radiation detecting cassette 24 includes the power supply 90 and the battery 92, the battery 92 can be charged by excess electric power produced when the radiation detecting cassette 24 is energized by the power supply 90. Similarly, electric power from the detecting LC resonator 94 can be supplied to and stored in the battery 92. Stated otherwise, the radiation detecting cassette 24 needn't only perform the process of charging the battery 92, but rather, the battery 92 can be charged whenever the radiation detecting cassette 24 is in use.

When the radiation detecting cassette 24 is used, information indicative of whether a magnetic field M from the LC resonator 84 exists or not (i.e., whether outputting is appropriate or not) is supplied by the energy detector 96. If the power feeder 25 fails, or the magnetic field M from the LC resonator 84 becomes unstable while the radiation detecting cassette 24 is being used (while radiographic image information is being captured), then the energy detector 96 does not detect the desired magnetic field M. In this case, the operation manager (power supply selector) 102 changes from the power supply 90 to the battery 92, for thereby energizing the radiation detecting cassette 24 as a whole and also for individually energizing the radiation detector 40, the cassette controller 46, and the transceiver 48. Since the radiation detecting cassette 24 is prevented from failing to operate while radiographic image information is being captured, and can continuously be used, the image capturing process as well as the surgical operation are prevented from becoming interrupted. In other words, since the radiation detecting cassette 24 uses both the power supply 90 and the battery 92, the radiation detecting cassette 24 can be energized with increased stability. When necessary, the radiation detecting cassette 24 may be energized by the battery 92 only, without the need for the power feeder 25. Of course, when radiographic images are not being captured, only a process of charging the battery 92 can be performed by the power feeder 25, or by any of other similar power feeders.

If the energy detector 96 does not detect the desired magnetic field M, the data manager 106 transmits a wireless feeding non-enable signal to the cassette information manager 126 via the transceivers 48, 116. The transceiver 116 sends the wireless feeding non-enable signal to the receiver 110, so that a wireless feeding non-enabled state can be displayed on the display unit (indicator) 114 in order to be viewed by the surgeon or the like.

In the radiographic image capturing system 10B, since cables for transmitting and receiving signals are not connected between the radiation detecting cassette 24 and the console 28, between the image capturing apparatus 22 and the console 28, between the power feeder 25 and the console 28, or between the console 28 and the display device 26, no cables are placed on the floor of the operating room 12, and thus such cables do not present an obstacle to operations performed by the surgeon 18, etc.

Figure 8:
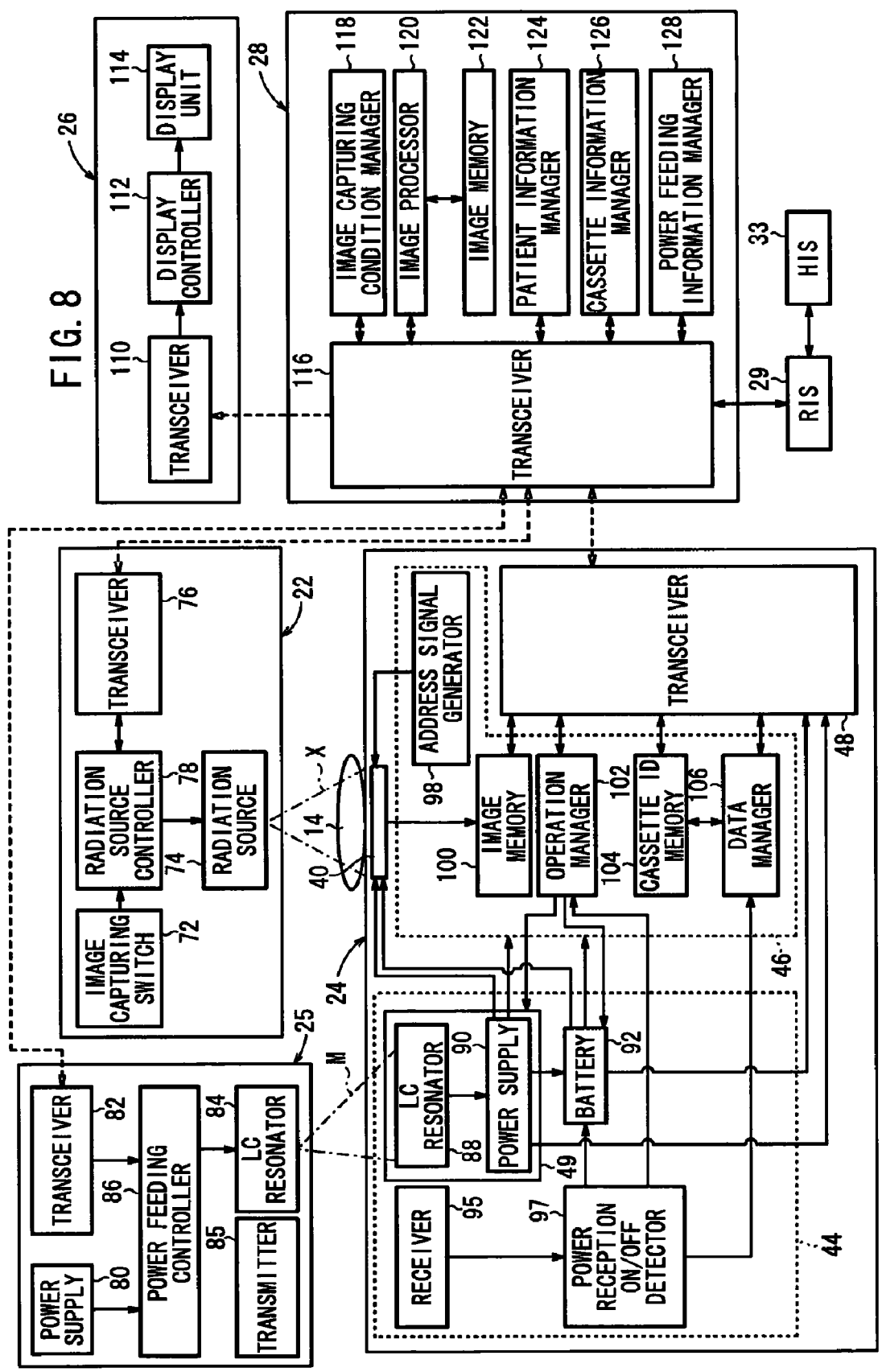
FIG. 8 is a block diagram of a modification of the radiographic image capturing system shown in FIG. 5.

The radiographic image capturing system 10B employs the detecting LC resonator 94 and the energy detector as a power feeding on/off detector, in order to detect whether the radiation detecting cassette 24 resides within the feeding area of the power feeder 25, i.e., whether the radiation detecting cassette 24 is in a power receiving area of the power feeder 25 or not. Alternatively, as shown in FIG. 8, a radiographic image capturing system 10Ba may be configured such that the power feeder 25 includes a transmitter 85, whereas the radiation detecting cassette 24 includes a receiver 95 and a power reception on/off detector 97, instead of the detecting LC resonator 94 and the energy detector 96.

The transmitter 85 sends a signal indicative of a feeding area to the receiver 95 by way of wireless communications, which do not affect the wireless communications between the transceivers 48, 116, by providing directivity and limiting communication ranges. An LED (light emitter) may be used instead of the transmitter 85, and a light detector may be used instead of the receiver 95, for performing a similar detecting process.

The radiographic image capturing system 10B according to the second embodiment is not limited to the features described above, but may be freely modified to include other various arrangements.

More specifically, the power feeder 25 may be of any type, insofar as the power feeder 25 can supply electric power wirelessly (contactlessly) to the radiation detecting cassette 24. For example, instead of the LC resonators 84, 88 and the detecting LC resonators 94, the power feeder 25 may comprise components made of dielectric materials utilizing an electric field rather than a magnetic field, and hence the power feeder 25 may be other than a resonant wireless power feeder. Stated otherwise, the supplied energy, which is converted from the electric energy supplied from the power feeder 25 to the radiation detecting cassette 24, may be optical energy, thermal energy, or other types of energy.

A radiographic image capturing system 10C according to a third embodiment will be described below with reference to FIGS. 9 through 12.

Figure 9:
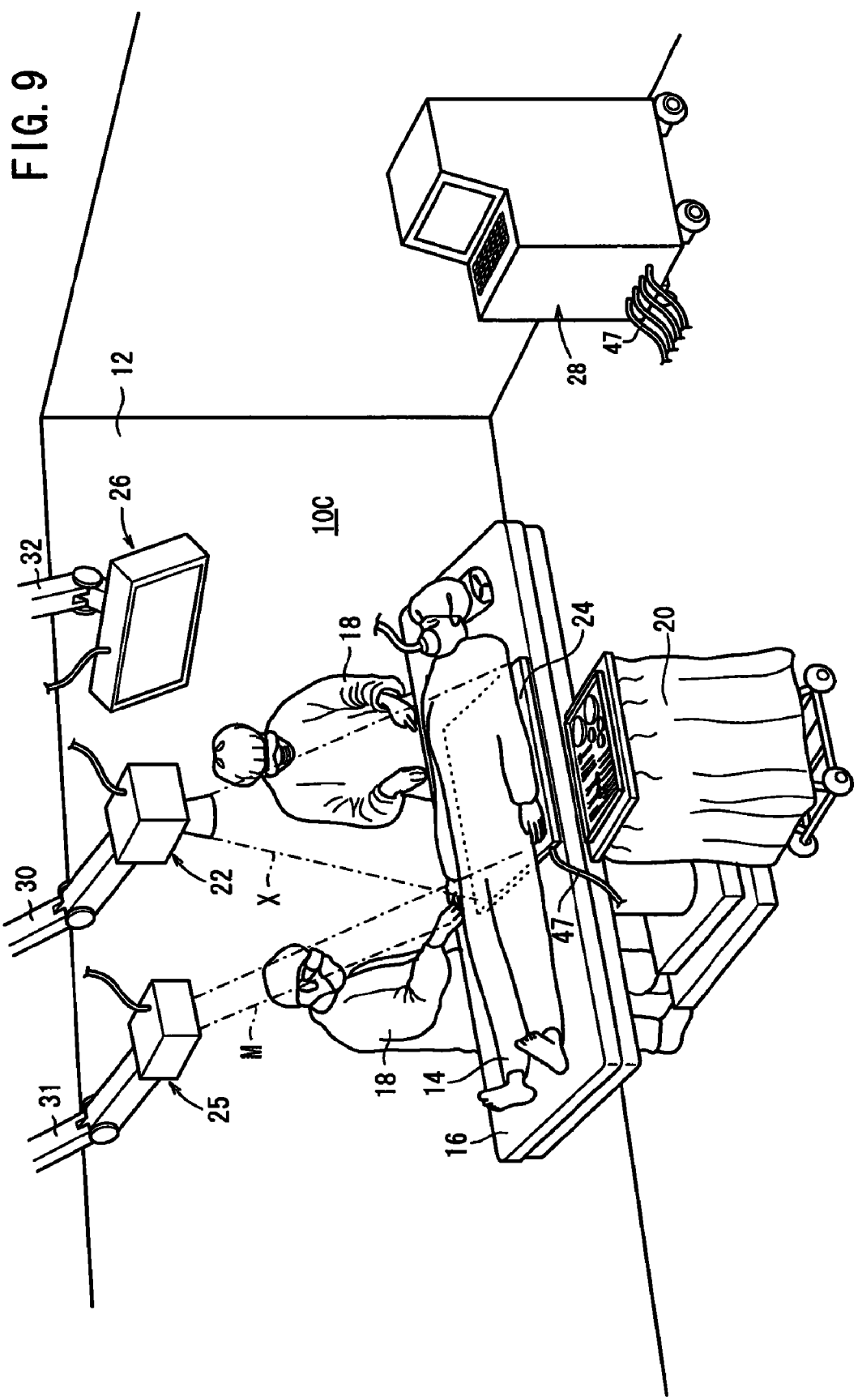
FIG. 9 is a perspective view of an operating room incorporating a radiographic image capturing system therein according to a third embodiment of the present invention.

As shown in FIG. 9, the radiographic image capturing system 10C according to the third embodiment differs from the radiographic image capturing system 10B according to the second embodiment (FIGS. 5 through 8), in that the image capturing apparatus 22, the radiation detecting cassette 24, the power feeder 25, the display device 26, and the console 28 are connected by power cables (power supply system) and signal cables (signal system) for sending and receiving signals therethrough.

Figure 10:
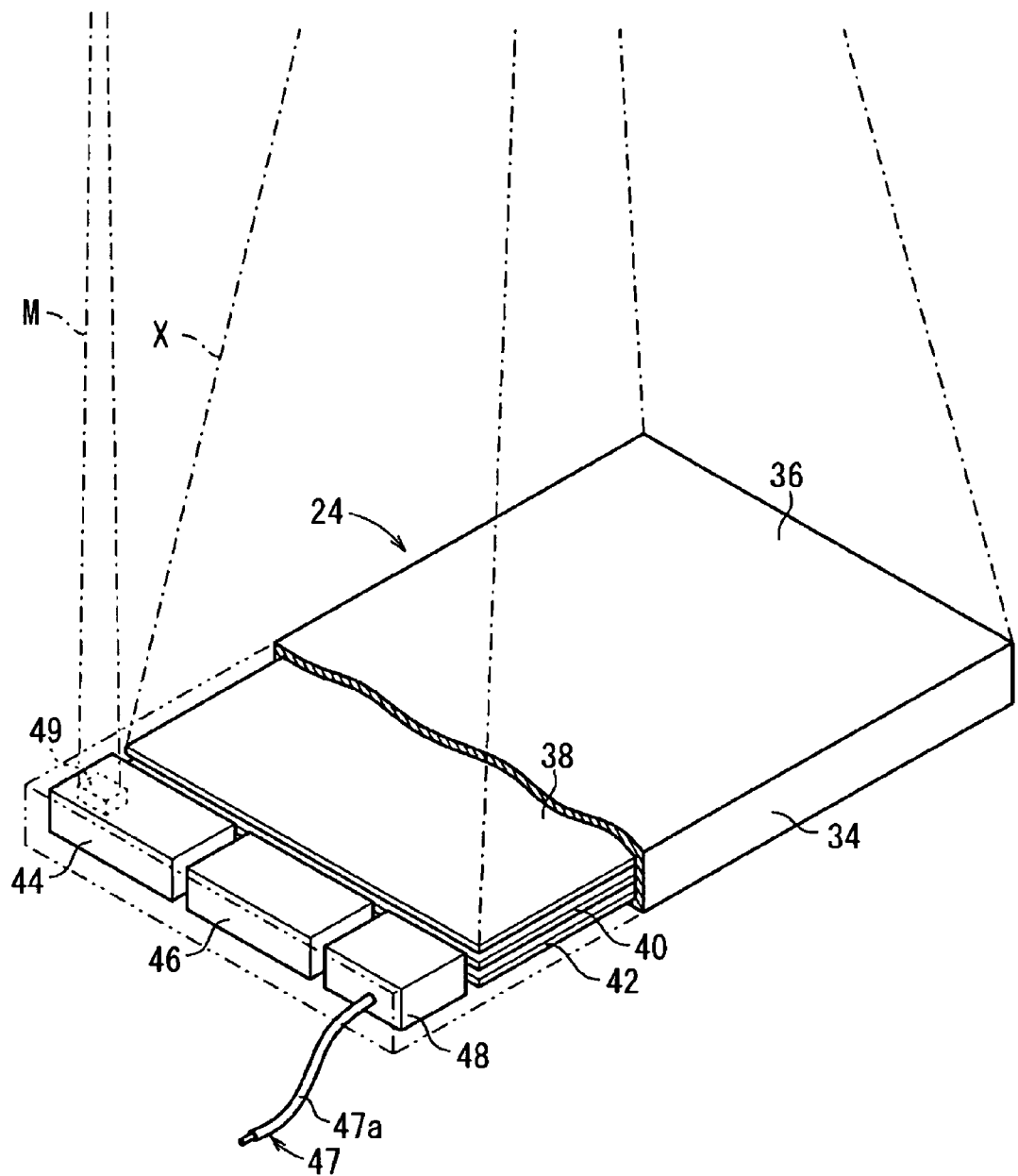
FIG. 10 is a perspective view, partially cut away, of a radiation detecting cassette shown in FIG. 9.

FIG. 10 is a perspective view, partially cut away, of the radiation detecting cassette 24 shown in FIG. 9. The transceiver 48 sends and receives signals to and from the console 28, including information of the radiation X detected by the radiation detector 40, through a signal cable (signal line) 47.

Figure 11:
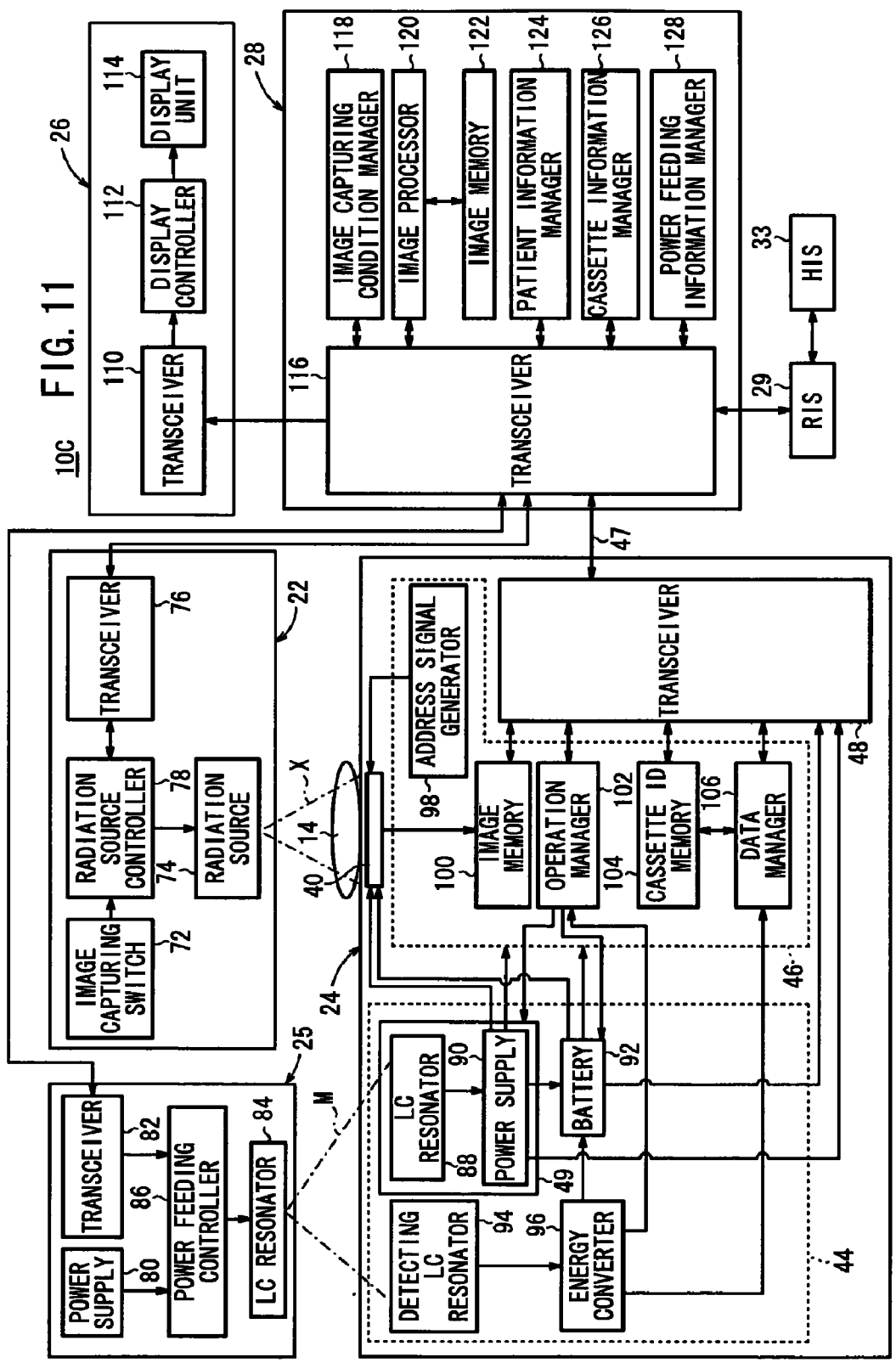
FIG. 11 is a block diagram of the radiographic image capturing system shown in FIG. 9.

FIG. 11 is a block diagram of the radiographic image capturing system 10C. The transceiver 48 receives a transmission request signal and ID information of the power feeder 25 from the console 28 through the signal cable 47, and sends radiographic image information stored in the image memory 100, cassette ID information stored in the cassette ID memory 104, and a wireless feeding enable signal from the data manager 106 based on the feeding area detection signal from the energy detector 96, to the console 28 through the signal cable 47.

The radiographic image capturing system 10C thus constructed according to the third embodiment operates basically in the same manner as the radiographic image capturing system 10B according to the second embodiment (FIGS. 5 through 8). However, in order to capture a radiographic image during a surgical operation, the data manager 106 receives ID information of the power feeder 25, which is stored in the power feeding information manager 128 of the console 28, via the transceivers 82, 116 and through the signal cable 47, and transmits a wireless feeding enable signal to the cassette information manager 126 via the transceivers 48, 116 and through the signal cable 47. The radiographic image information stored in the image memory 100 is transmitted to the console 28 via the transceiver 48 through the signal cable 47.

As described above, the radiographic image capturing system 10C according to the third embodiment includes the power feeder 25 disposed in a position capable of wirelessly feeding power to the radiation detecting cassette 24 at all times while the radiation detecting cassette 24 is being used (i.e., while a radiographic image is captured). Therefore, the radiographic image capturing system 10C can capture radiographic images without requiring power cables to be connected to the radiation detecting cassette 24, except for the signal cable 47. Not only the radiation detecting cassette 24, but also the system as a whole, can be handled with ease. Furthermore, the process of capturing radiographic images and surgical operations are effectively prevented from becoming interrupted due to an excessively low remaining power level in the battery of the radiation detecting cassette 24.

The radiographic image information acquired and converted by the radiation detector 40 is transmitted from the radiation detecting cassette 24 to the console 28 in a wired fashion through the signal cable 47, which interconnects the transceivers 48, 116. Consequently, the transmitted radiographic image information is reliably prevented from being adversely affected by radio disturbance and noise from other electronic devices, as compared to a case in which the radiographic image information is transmitted wirelessly as disclosed in Patent Document 4. Therefore, radiographic images can be generated highly accurately and precisely. Since no power cables, except for the signal cable 47, are connected between the radiation detecting cassette 24 and the console 28, cables connected to the radiation detecting cassette 24 can be kept to a minimum, and the radiation detecting cassette 24 can be handled with increased ease, while at the same time radiation images are prevented from becoming degraded.

According to the third embodiment, the radiation detecting cassette 24 is wirelessly fed power by the power feeder 25 in order to increase ease with which the radiation detecting cassette 24 is handled. Inasmuch as the magnetic field M applied from the power feeder 25 to the radiation detecting cassette 24 is reliably prevented from adversely affecting the radiographic image information, use of the signal cable 47 to send and receive radiographic image information is highly effective. The signal cable 47 connected from the radiation detecting cassette 24 to the console 28 is surrounded by a noise prevention shield 47a (see FIG. 10), having a twisted pair of internal signal lines and covered with a grounded sheath. Therefore, the adverse effect that electromagnetic waves from other electronic devices have on the signal cable 47, which transmits radiographic image information, etc., is further reduced, and noise is effectively prevented from being added to the radiographic image information, thereby further reducing image degradation.

With the radiographic image capturing system 10C, when the radiation detecting cassette 24 is placed in the feeding area of the power feeder 25, the radiation detecting cassette 24 and the power feeder 25 automatically exchange information with each other through the console 28, whereby the radiation detecting cassette 24 is brought into a state capable of capturing radiographic images. Consequently, the radiation detecting cassette 24 does not need to be activated in advance in a preparatory state in order to capture radiographic images, using the battery 92, etc., and the radiation detecting cassette 24 is not required to have a manual power supply switch. Wasteful power consumption and malfunctioning is avoided, and the surgeon 18 or the radiological technician can be prevented from making a mistake, such as not capturing a radiographic image by forgetting to operate a manual power supply switch. Moreover, since information is sent and received between the console 28 and the radiation detecting cassette 24 in a wired fashion through the signal cable 47, the wireless feeding enable signal can accurately and reliably be sent from the radiation detecting cassette 24 to the console 28 together with the radiographic image information. Accordingly, the radiographic image capturing system 10C including the radiation detecting cassette 24 can be handled with greater ease.

Figure 12:
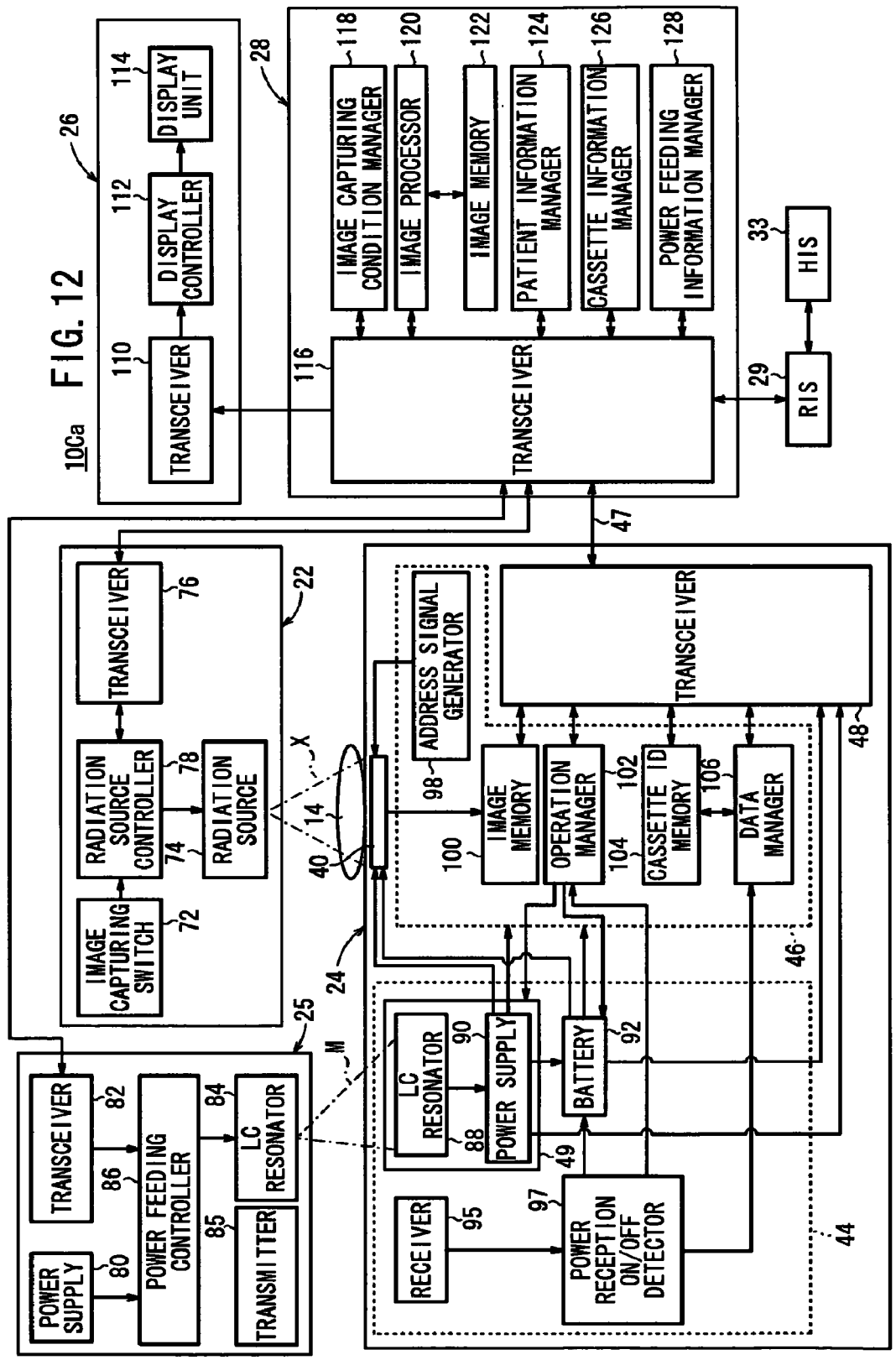
FIG. 12 is a block diagram of a modification of the radiographic image capturing system shown in FIG. 9.

As shown in FIG. 12, a radiographic image capturing system 10Ca may be configured such that the power feeder 25 includes a transmitter 85, whereas the radiation detecting cassette 24 includes a receiver 95 and a power reception on/off detector 97, instead of the detecting LC resonator 94 and the energy detector 96.

The transmitter 85 sends a signal indicative of a feeding area to the receiver 95 by way of wireless communications, which do not affect other wireless communications, by providing directivity and limiting communication ranges. An LED (light emitter) may be used instead of the transmitter 85, and a light detector may be used instead of the receiver 95, for performing a similar detecting process.

The radiographic image capturing systems 10A through 10C according to the first through third embodiments are not limited to the embodiments described above, but alternatively may be arranged in the following manner:

When the radiation detecting cassette 24 is used in an operating room or the like, blood stains and contaminants may be applied to the radiation detecting cassette 24. Thus, the radiation detecting cassette 24 may be of a water-resistant, sealed structure so that the radiation detecting cassette 24 can be sterilized and cleaned in order to remove such blood stains and contaminants, for enabling repetitive use thereof.

The radiation detecting cassette 24 is not limited to being used in an operating room 16, but may also be used in combination with medical examinations and doctor's visits to patient rooms within the hospital.

The radiation detecting cassette 24 may communicate with an external device (i.e., the radiation detecting cassette 24 may be wirelessly fed in the radiographic image capturing system 10C) by way of optical wireless communications using infrared rays or the like, rather than by typical wireless communications using radio waves.

Figure 13:
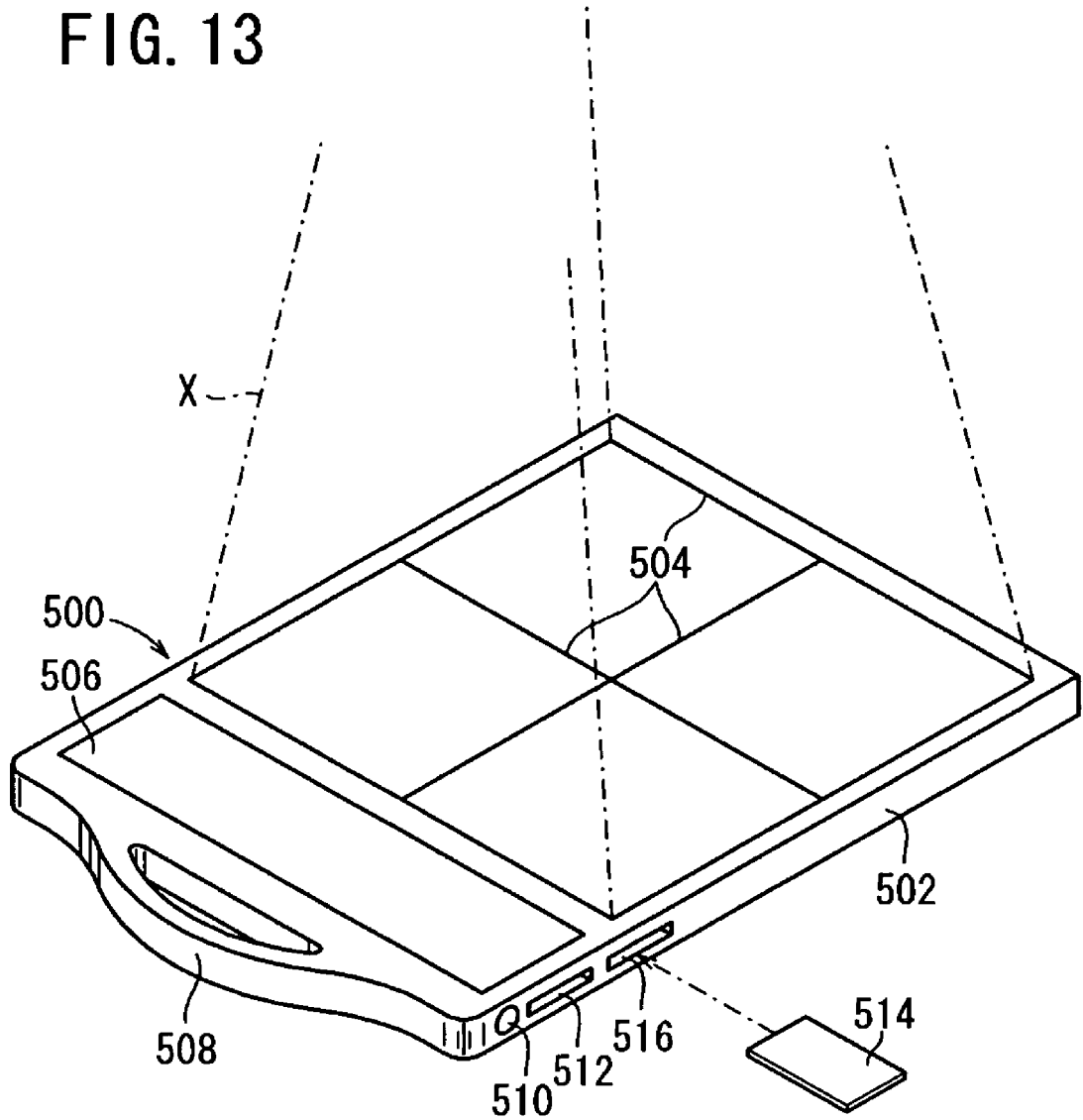
FIG. 13 is a perspective view of another radiation detecting cassette.

A radiation detecting cassette 500 shown in FIG. 13 is even more preferable.

The cassette 500 includes guide lines 504, which are drawn on the irradiated surface of a casing 502 and serve as reference marks for an image capturing area and an image capturing position. Using the guide lines 504, the subject to be imaged, such as the patient 14, can be positioned with respect to the cassette 500, and the range in which radiation is to be applied to the cassette 500 can be determined, for thereby recording radiation image information within an appropriate image capturing area of the cassette 500.

The cassette 500 also has a display unit 506 positioned outside of the image capturing area for displaying various items of information concerning the cassette 500. Specifically, the display unit 506 displays ID information of the subject, e.g., the patient 14, whose radiation image is recorded in the cassette 500, the number of times that the cassette 500 has been used, an accumulated exposure dose, the charged state (remaining power level) of the power source 44 (battery 92) housed in the cassette 500, image capturing conditions for the radiation image information, and a positioning image representing the patient 14 positioned with respect to the cassette 500, etc. The radiological technician can confirm the patient 14 based on the ID information displayed on the display unit 506, and also can confirm in advance that the cassette 500 is in a usable state. Further, the radiological technician can position the desired area to be imaged of the patient 14 with respect to the cassette 500 based on the displayed positioning image, in order to capture optimum radiation image information in the cassette 500.

The cassette 500 includes a handle 508, which can be gripped by the user to handle and carry the cassette 500 with ease.

The cassette 500 also has an input terminal 510 for connection to an AC adapter, a USB (Universal Serial Bus) terminal 512, and a card slot 516 for receiving a memory card 514, all of which are provided on a side wall of the casing of the cassette 500.

When the charging capacity of the power source 44 (battery 92) housed in the cassette 500 is low, or when there is not enough time to charge the power source 44 (battery 92), an AC adapter may be connected to the input terminal 510 in order to supply electric power from an external circuit, thereby making the cassette 500 immediately operable.

The USB terminal 512 or the card slot 516 can be used when the cassette 500 is unable to send and receive information to and from an external device, such as the console 28 or the like, by way of wireless communications. More specifically, when a USB cable connected to the external device is connected to the USB terminal 512, the cassette 500 can send and receive information to and from the external device by way of wired communications through the USB terminal 512 and the USB cable. Alternatively, the memory card 514 may be inserted into the card slot 516, and essential information from the cassette 500 may be recorded into the memory card 514. Thereafter, the memory card 514 is disconnected and connected to the external device in order to send information to the external device.

In FIG. 13, the signal cable 47 of the radiographic image capturing system 10C has been omitted from illustration.

Figure 14:
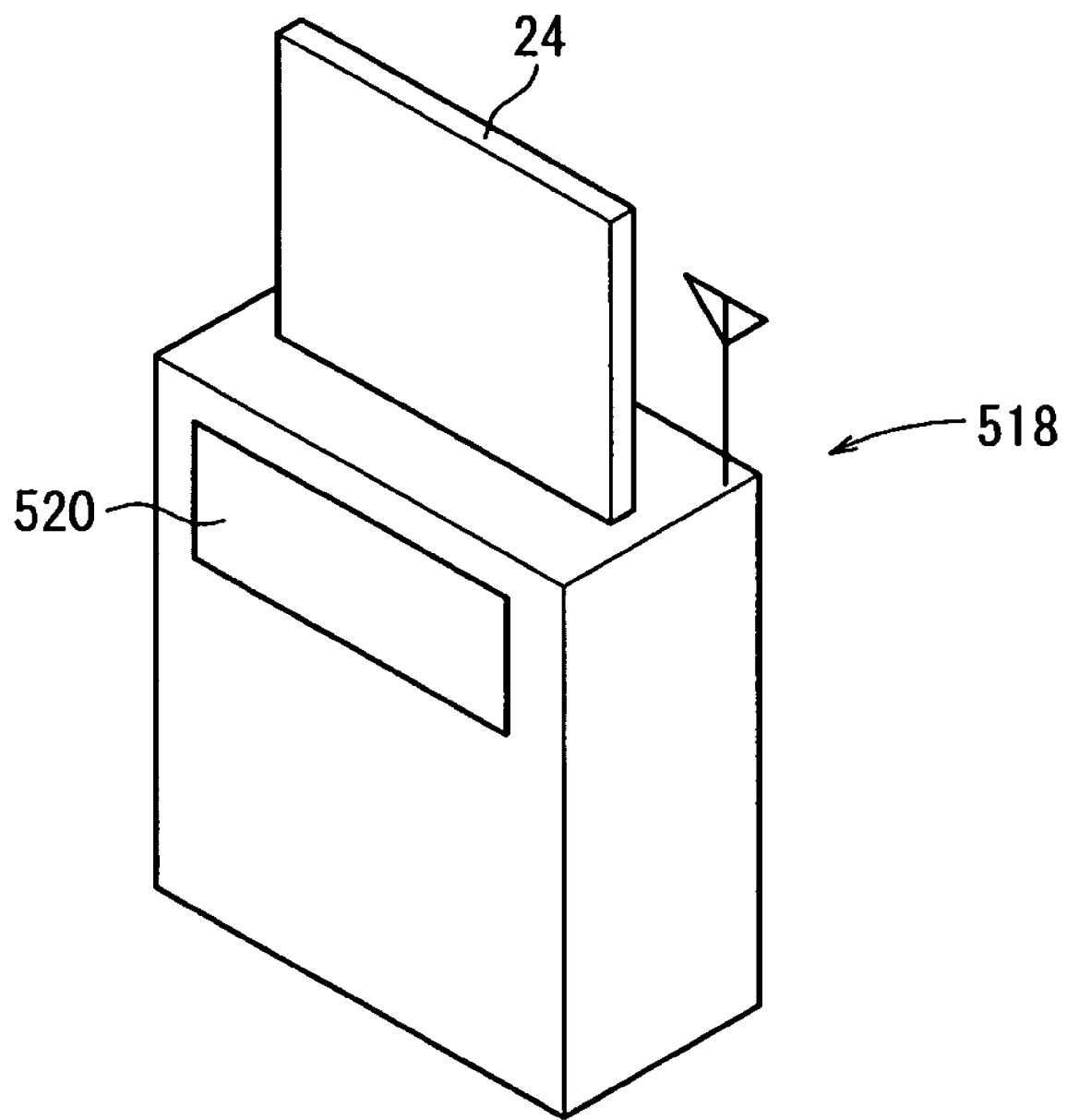
FIG. 14 is a perspective view of a cradle for charging a battery in the radiation detecting cassette.

As shown in FIG. 14, a cradle 518 for receiving the radiation detecting cassette 24 and charging the power supply (battery) 44 housed in the radiation detecting cassette 24 is positioned in an operating room 12 or at a desired location in the hospital. The cradle 518 is not only capable of charging the power supply (battery) 44, but also has a wireless or wired communication function in order to send and receive necessary information to and from an external device, such as the RIS 29, the HIS 31, the console 28, or the like. Information that is sent from the cradle 518 may include radiation image information, which is recorded in the cassette 24 loaded in the cradle 518.

The cradle 518 includes a display unit 520 for displaying the charged state of the cassette 24, together with other necessary information including radiation image information acquired from the cassette 24.

A plurality of cradles 518 may be connected to a network, and charged states of the cassettes 24 loaded in the respective cradles 518 may be retrieved through the network, so that the user can confirm locations of cassettes 24 that are sufficiently charged and thus capable of being used, based on the retrieved charged states.

The radiation detecting cassettes and the radiographic image capturing systems according to the present invention are not limited to the above-described embodiments, various other arrangements may be employed therein without departing from the scope of the invention.

The invention claimed is:

1. A radiation detecting cassette comprising:
   a radiation conversion panel for detecting radiation that has passed through a subject and converting the detected radiation into radiographic image information;
   wireless communicating means for performing wireless communications with an external circuit;
   wireless communications control means for controlling the wireless communicating means;
   exposure detecting means for detecting application of the radiation to the radiation conversion panel and outputting a detected result as an exposure detection signal to the wireless communications control means;
   address signal generating means for supplying address signals to the radiation conversion panel for enabling the radiation conversion panel to convert the detected radiation into the radiographic image information;
   a conversion detector which detects the address signals and outputs a detected result as a conversion detection signal to the wireless communications control means; and
   a power supply for energizing the radiation conversion panel, the exposure detecting means, the conversion detector, the wireless communicating means, and the wireless communications control means,
   wherein the wireless communications control means controls the wireless communicating means to inhibit transmission of the radiographic image information to an external circuit by way of the wireless communications and/or to inhibit supply of electric power from an external circuit to the power supply by way of the wireless communications.

2. A radiation detecting cassette according to claim 1, wherein the wireless communicating means performs UWB wireless communications with the external circuit.

3. A radiation detecting cassette according to claim 1, wherein the exposure detecting means specifies a given pixel among a plurality of pixels of the radiation conversion panel, detects application of the radiation to the radiation conversion panel based on a dose of the radiation detected by the specified pixel, and outputs a detected result as the exposure detection signal to the wireless communications control means.

4. A radiation detecting cassette according to claim 1, wherein the conversion detector detects the address signals and outputs the detected result when the radiation conversion panel converts the detected radiation into the radiographic image information upon supply of the address signals from the address signal generating means to the radiation conversion panel.

5. A radiographic image capturing system comprising a radiation detecting cassette, a radiation source for outputting the radiation, and a control device for controlling the radiation source and the radiation detecting cassette
   wherein the radiation detecting cassette includes:
   a radiation conversion panel for detecting radiation that has passed through a subject and converting the detected radiation into radiographic image information;
   wireless communicating means for performing wireless communications with an external circuit;
   wireless communications control means for controlling the wireless communicating means;
   exposure detecting means for detecting application of the radiation to the radiation conversion panel and outputting a detected result as an exposure detection signal to the wireless communications control means;
   address signal generating means for supplying address signals to the radiation conversion panel for enabling the radiation conversion panel to convert the detected radiation into the radiographic image information;
   a conversion detector which detects the address signals and outputs a detected result as a conversion detection signal to the wireless communications control means; and
   a power supply for energizing the radiation conversion panel, the exposure detecting means, the conversion detector, the wireless communicating means, and the wireless communications control means,
   wherein the wireless communications control means controls the wireless communicating means to inhibit transmission of the radiographic image information to an external circuit by way of the wireless communications and/or to inhibit supply of electric power from an external circuit to the power supply by way of the wireless communications.

6. A radiographic image capturing system comprising:
a radiation detecting cassette including a radiation conversion panel for detecting radiation that has passed through a subject and converting the detected radiation into radiographic image information, and transmitting means connected to the radiation conversion panel, for transmitting the radiographic image information to an image processing means; and
a power feeder for wirelessly feeding power to the radiation detecting cassette,
wherein the power feeder includes electric power transmitting means for converting electric energy and wirelessly supplying the converted energy to the radiation detecting cassette;
the radiation detecting cassette includes an energy converter for converting the energy supplied from the electric power transmitting means back into electric energy; and
the electric power transmitting means is disposed in a state for wirelessly feeding power to the energy converter of the radiation detecting cassette, which is disposed in a state for capturing a radiographic image of the subject.

7. A radiographic image capturing system according to claim 6, wherein the radiation detecting cassette includes an electric power reception on/off detector for detecting whether the radiation detecting cassette has been placed in an area capable of receiving energy supplied from the electric power transmitting means.

8. A radiographic image capturing system comprising:
a radiation detecting cassette including a radiation conversion panel for detecting radiation that has passed through a subject and converting the detected radiation into radiographic image information, and transmitting means connected to the radiation conversion panel, for transmitting the radiographic image information to an image processing means; and
a power feeder for wirelessly feeding power to the radiation detecting cassette,
wherein the power feeder includes electric power transmitting means for converting electric energy and wirelessly supplying the converted energy to the radiation detecting cassette; and
the radiation detecting cassette includes an energy converter for converting the energy supplied from the electric power transmitting means back into electric energy, and an electric power reception on/off detector for detecting whether the radiation detecting cassette has been placed in an area capable of receiving energy supplied from the electric power transmitting means.

9. A radiographic image capturing system according to claim 8, wherein the radiation detecting cassette includes a battery for storing the electric energy converted back by the energy converter.

10. A radiographic image capturing system according to claim 9, further comprising:
a power supply selector for selecting the battery as a power supply for energizing the radiation detecting cassette if the electric power reception on/off detector detects that the radiation detecting cassette has been placed outside of the area capable of receiving energy supplied from the electric power transmitting means.

11. A radiographic image capturing system according to claim 8, wherein the radiation detecting cassette includes a controller for instructing the energy converter to start converting the energy back into the electric energy if the electric power reception on/off detector detects that the radiation detecting cassette has been placed in the area capable of receiving energy supplied from the electric power transmitting means.

12. A radiographic image capturing system according to claim 8, further comprising:
an indicator for externally indicating that the electric power reception on/off detector detects that the radiation detecting cassette has been placed outside of the area capable of receiving energy supplied from the electric power transmitting means.

13. A radiation detecting cassette comprising:
a radiation conversion panel for detecting radiation that has passed through a subject and converting the detected radiation into radiographic image information;
transmitting means connected to the radiation conversion panel, for transmitting the radiographic image information to an image processing means;
an energy converter for converting wirelessly supplied energy converted from electric energy back into electric energy; and
an electric power reception on/off detector for detecting whether the radiation detecting cassette has been placed in an area capable of receiving the wirelessly supplied energy.

14. A radiographic image capturing system comprising:
a radiation detecting cassette including a radiation conversion panel for detecting radiation that has passed through a subject and converting the detected radiation into radiographic image information, and transmitting means connected to the radiation conversion panel, for transmitting the radiographic image information to an image processing means; and
a power feeder for feeding power to the radiation detecting cassette,
wherein the transmitting means transmits the radiographic image information to the image processing means in a wired fashion through a signal line;
the power feeder wirelessly feeds power to the radiation detecting cassette; and
the radiation detecting cassette includes an energy converter for converting wirelessly supplied energy converted from electric energy back into electric energy, and
an electric power reception on/off detector for detecting whether the radiation detecting cassette has been placed in an area capable of receiving the wirelessly supplied energy.

15. A radiographic image capturing system according to claim 14, wherein the power feeder includes electric power transmitting means for converting electric energy and wirelessly supplying the converted energy to the radiation detecting cassette.

16. A radiographic image capturing system according to claim 15, wherein the radiation detecting cassette includes data control means for receiving identification data of the power feeder and transmitting a wireless feeding enable signal to an external control device via the transmitting means and the signal line if the electric power reception on/off detector detects that the radiation detecting cassette has been placed in the area capable of receiving energy supplied from the electric power transmitting means; and
the control device receives the wireless feeding enable signal from the radiation detecting cassette and thereafter transmits a power feeding start signal to the power feeder that corresponds to the identification data.

* * * * *

UNITED STATES PATENT AND TRADEMARK OFFICE
CERTIFICATE OF CORRECTION

| | | |
|---|---|---|
| PATENT NO. | : 8,357,908 B2 | Page 1 of 1 |
| APPLICATION NO. | : 12/452864 | |
| DATED | : January 22, 2013 | |
| INVENTOR(S) | : Takeshi Kuwabara | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 444 days.

Signed and Sealed this
Seventeenth Day of March, 2015

Michelle K. Lee
*Director of the United States Patent and Trademark Office*